US012018274B2

(12) United States Patent
Thompson

(10) Patent No.: US 12,018,274 B2
(45) Date of Patent: *Jun. 25, 2024

(54) COMPOSITIONS AND METHODS FOR REGULATING PRODUCTION OF A FUSION PROTEIN AND RIBONUCLEIC ACID

(71) Applicant: Wyvern Pharmaceuticals Inc., Calgary (CA)

(72) Inventor: Bradley G. Thompson, Calgary (CA)

(73) Assignee: Wyvern Pharmaceuticals Inc., Calgary (CA)

( * ) Notice: Subject to any disclaimer, the term of this patent is extended or adjusted under 35 U.S.C. 154(b) by 0 days.

This patent is subject to a terminal disclaimer.

(21) Appl. No.: 17/867,881

(22) Filed: Jul. 19, 2022

(65) Prior Publication Data

US 2024/0026377 A1 Jan. 25, 2024

(51) Int. Cl.

| | |
|---|---|
| ***C12N 15/86*** | (2006.01) |
| ***C07K 14/705*** | (2006.01) |
| ***C12N 15/113*** | (2010.01) |
| ***C12N 15/62*** | (2006.01) |
| *A61K 48/00* | (2006.01) |

(52) U.S. Cl.

CPC ........ *C12N 15/86* (2013.01); *C07K 14/70521* (2013.01); *C12N 15/1136* (2013.01); *C12N 15/62* (2013.01); *A61K 48/00* (2013.01); *C07K 2319/30* (2013.01); *C12N 2310/141* (2013.01); *C12N 2750/14143* (2013.01); *C12N 2750/14171* (2013.01)

(58) Field of Classification Search

CPC .... C12N 15/86; C12N 15/1136; C12N 15/62; C12N 2310/141; C12N 2750/14143; C12N 2750/14171; C07K 14/70521; C07K 2319/30; A61K 48/00

See application file for complete search history.

*Primary Examiner* — Titilayo Moloye

(74) *Attorney, Agent, or Firm* — Gowling WLG (Canada) LLP

(57) ABSTRACT

The present disclosure relates to one or more agents, therapies, treatments, and methods of use of the agents and/or therapies and/or treatments for increasing production of a belatacept-similar protein and micro-RNA associated with decreasing production of tumor necrosis factor alpha. Embodiments of the present disclosure can be used as a therapy or a treatment for a subject that has a condition whereby the subject's immune system is, or is likely to become, dysregulated and where the production of the belatacept-similar protein and decreased production of tumor necrosis factor alpha may be of therapeutic benefit.

4 Claims, 19 Drawing Sheets

Specification includes a Sequence Listing.

SEQ ID NO. 1

SEQ ID NO. 1

SEQ ID NO. 1

```
                                                                    AfeI
ccgggtttggcgcctccgcggggcgccccctcctcacggcgagcgctgccacgtcagacgaag
++++++++++++++++++++++++++++++++++++++++++++++++++++++++++++++++    975
ggcccaaaccgcggaggggcgccgcggggggaggagtgccgctcgcgacggtgcagtctgcttc
                           CASI promoter

ggcgcagcgagcgtcctgatccttccgcccggacgctcaggacagcggcccgctgctcataagac
++++++++++++++++++++++++++++++++++++++++++++++++++++++++++++++++   1040
ccgcgtcgctcgcaggactaggaaggcgggcctgcgagtcctgtcgccgggcgacgagtattctg
                           CASI promoter

tcggccttagaaccccagtatcagcagaaggacatttaggacgggacttgggtgactctagggc
++++++++++++++++++++++++++++++++++++++++++++++++++++++++++++++++   1105
agccggaatcttggggtcatagtcgtcttcctgtaaatcctgcctgaacccactgagatccg
                           CASI promoter

actggttttctttccagagagcggaacaggcgaggaaaagtagtcccttctcggcgattctgcgg
++++++++++++++++++++++++++++++++++++++++++++++++++++++++++++++++   1170
tgaccaaaagaaaggtctctcgccttgtccgctcctttcatcagggaagagccgctaagacgcc
                           CASI promoter

agggatctccgtggggcggtgaacgccgatgatgcctactaaccatgttcatgtttctttt
++++++++++++++++++++++++++++++++++++++++++++++++++++++++++++++++   1235
tccctagaggcaccccgccacttgcggctactacggagatgattggtacaagtacaaaagaaaa
                           CASI promoter

          PmeI            Acc65I   KpnI
ttttctacaggtcctgggtgacgaacagGGTACCGCCACCATGGCCACCGGCTCTCGCACAAGCC
++++++++++++++++++++++++++++++++++++++++++++++++++++++++++++++++   1300
aaaagatgtccaggaccactgcttgtcCCATGGCGGTGGTACCGGTGGCCGAGAGCGTGTTCGG
                                              1            5
                                              M  A  T  G  S  R  T  S
                    CASI promoter       KpnI
                                              HGH signal peptide (mouse codon optimized)

                                                                   PmlI
                                                                   BstXI
TGCTGCTGGCTTTCGGACTGCTGTGCCTGCCTTGGCTCCAGGAGGGCTCCGCCA T CACGTGGCC
++++++++++++++++++++++++++++++++++++++++++++++++++++++++++++++++   1365
ACGACGACCGAAAGCCTGACGACACGGACGGAACCGAGGTCCTCCCGAGGCGG T A GTGCACCGG
     10             15            20           25           1
     L  L  L  A  F  G  L  L  C  L  P  W  L  Q  E  G  S  A  M  H  V  A
              HGH signal peptide (mouse codon optimized)

CAGCCTGCTGTGGTACTGGCCAGCAGCCGAGGCATCGCCAGCTTTGTGTGTGAGTATGCATCTCC
++++++++++++++++++++++++++++++++++++++++++++++++++++++++++++++++   1430
GTCGGACGACACCATGACCGGTCGTCGGCTCCGTAGCGGTCGAAACACACACTCATACGTAGAGG
      5             10            15           20           25
      Q  P  A  V  V  L  A  S  S  R  G  I  A  S  F  V  C  E  Y  A  S  P
```

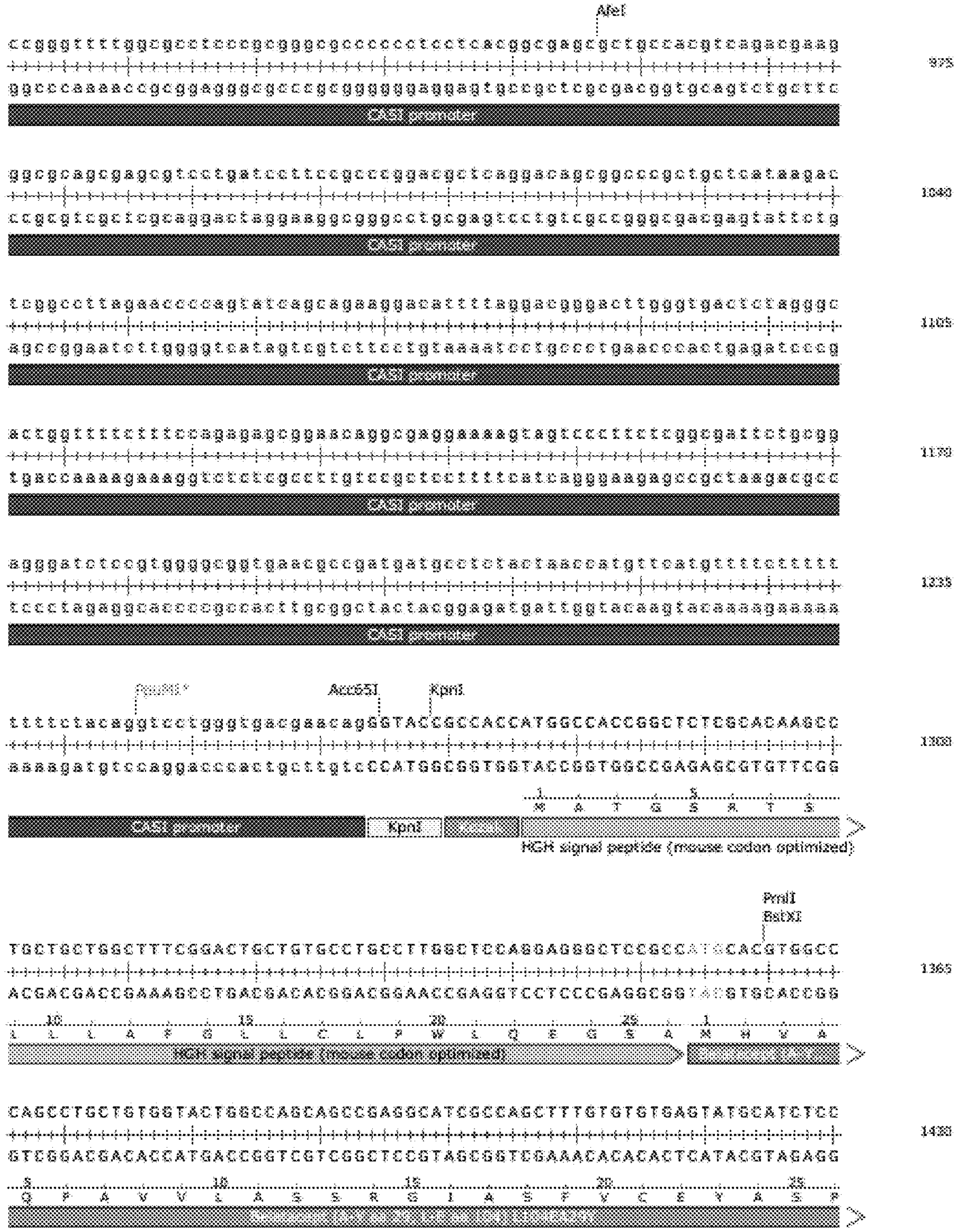

FIG. 4

SEQ ID NO. 1

SEQ ID NO. 1

SEQ ID NO. 1

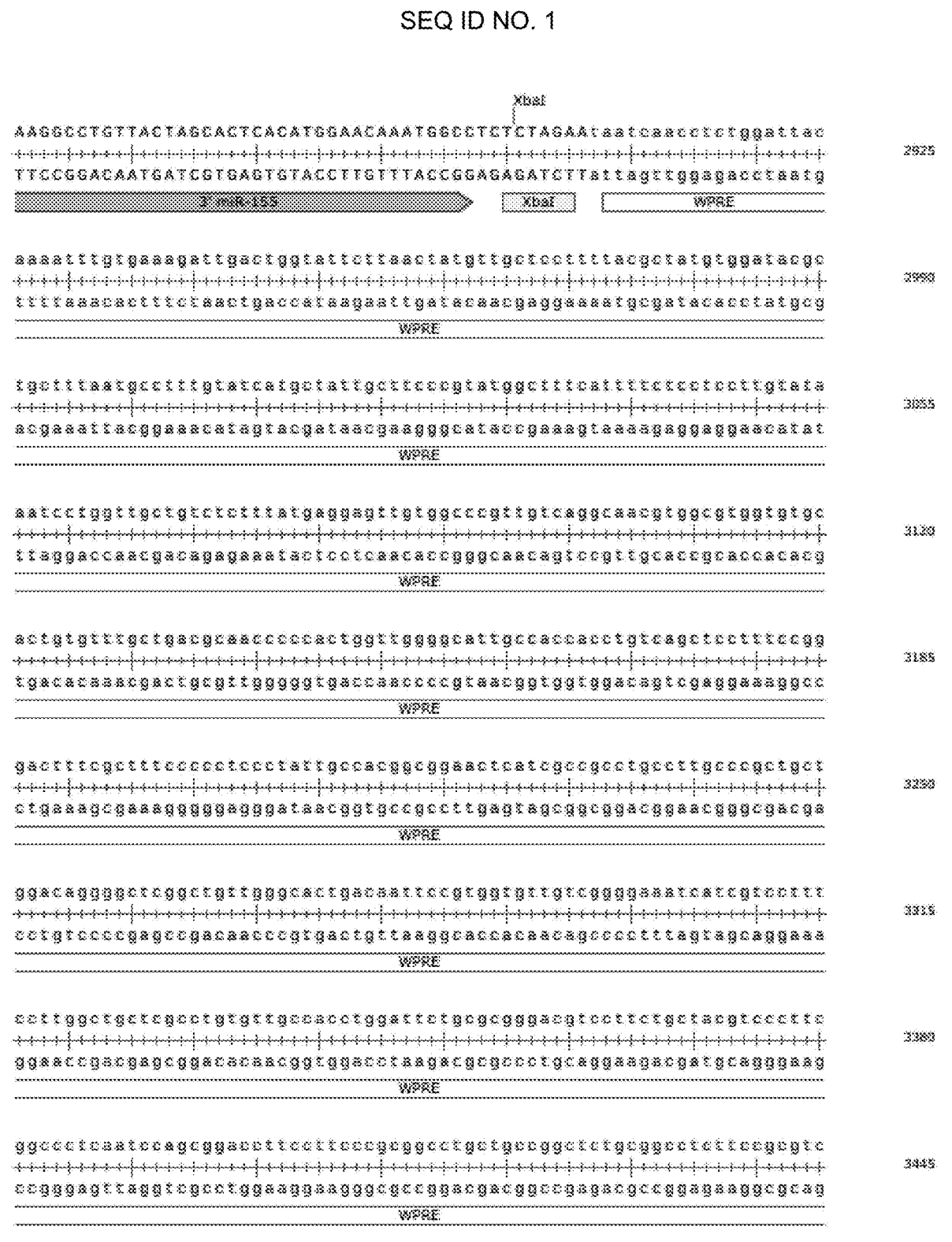

SEQ ID NO. 1

XbaI

AAGGCCTGTTACTAGCACTCACATGGAACAAATGGCCTCTCTAGAAtaatcaacctctggattac 2925

TTCCGGACAATGATCGTGAGTGTACCTTGTTTACCGGAGAGATCTTattagttggagacctaatg

3' miR-155 XbaI WPRE aaaatttgtgaaagattgactggtattcttaactatgttgctccttttacgctatgtggatacgc 2990 ttttaaacactttctaactgaccataagaattgatacaacgaggaaaatgcgatacacctatgcg

WPRE tgctttaatgcctttgtatcatgctattgcttcccgtatggctttcattttctcctccttgtata 3055 acgaaattacggaaacatagtacgataacgaagggcataccgaaagtaaaagaggaggaacatat

WPRE aatcctggttgctgtctctttatgaggagttgtggcccgttgtcaggcaacgtggcgtggtgtgc 3120 ttaggaccaacgacagagaaatactcctcaacaccgggcaacagtccgttgcaccgcaccacacg

WPRE actgtgtttgctgacgcaacccccactggttggggcattgccaccacctgtcagctcctttccgg 3185 tgacacaaacgactgcgttgggggtgaccaaccccgtaacggtggtggacagtcgaggaaaggcc

WPRE gactttcgctttccccctccctattgccacggcggaactcatcgccgcctgccttgcccgctgct 3250 ctgaaagcgaaagggggagggataacggtgccgccttgagtagcggcggacggaacgggcgacga

WPRE ggacaggggctcggctgttgggcactgacaattccgtggtgttgtcggggaaatcatcgtccttt 3315 cctgtccccgagccgacaacccgtgactgttaaggcaccacaacagcccctttagtagcaggaaa

WPRE ccttggctgctcgcctgtgttgccacctggattctgcgcgggacgtccttctgctacgtcccttc 3380 ggaaccgacgagcggacacaacggtggacctaagacgcgccctgcaggaagacgatgcagggaag

WPRE ggccctcaatccagcggaccttccttcccgcggcctgctgccggctctgcggcctcttccgcgtc 3445 ccgggagttaggtcgcctggaaggaagggcgccggacgacggccgagacgccggagaaggcgcag

WPRE

FIG. 8

SEQ ID NO. 1

```
                                                                HindIII
ttcgccttcgccctcagacgagtcggatctcccttgggccgcctccccgcctAAGCTTATCGAT
                                                                          3530
aagcggaagcgggagtctgctcagcctagagggaaacccggcggaggggcggaTTCGAATAGCTA
               WPRE

    BglII
ACCGTCGAGATCTAACTTGTTTATTGCAGCTTATAATGGTTACAAATAAAGCAATAGCATCACAA
                                                                          3575
TGGCAGCTCTAGATTGAACAAATAACGTCGAATATTACCAATGTTTATTTCGTTATCGTAGTGTT
                        SV40 poly(A) signal

                        BsmI
ATTTCACAAATAAAGCATTTTTTTCACTGCATTCTAGTTGTGGTTTGTCCAAACTCATCAATGTA
                                                                          3640
TAAAGTGTTTATTTCGTAAAAAAAGTGACGTAAGATCAACACCAAACAGGTTTGAGTAGTTACAT
                        SV40 poly(A) signal

TCTTATCATGTCTGGATCTCGACCTCGACTAGAGCATGGCTACGTAGATAAGTAGCATGGCGGGT
                                                                          3705
AGAATAGTACAGACCTAGAGCTGGAGCTGATCTCGTACCGATGCATCTATTCATCGTACCGCCCA
   SV40 poly(A) signal

TAATCATTAACTACAAGGAACCCCTAGTGATGGAGTTGGCCACTCCCTCTCTGCGCGCTCGCTCG
                                                                          3770
ATTAGTAATTGATGTTCCTTGGGGATCACTACCTCAACCGGTGAGGGAGAGACGCGCGAGCGAGC
                                                                  RBE

CTCACTGAGGCCGGGCGACCAAAGGTCGCCCGACGCCCGGGCTTTGCCCGGGCGGCCTCAGTGAG
                                                                          3835
GAGTGACTCCGGCCCGCTGGTTTCCAGCGGGCTGCGGGCCCGAAACGGGCCCGCCGGAGTCACTC

 RBE'                                                             RBE

CGAGCGAGCGCGCAGCTGGCGTAATAGCGAAGAGGCCCGCACCGATCGCCCTTCCCAACAGTTGC
                                                                          3900
GCTCGCTCGCGCGTCGACCGCATTATCGCTTCTCCGGGCGTGGCTAGCGGGAAGGGTTGTCAACG

    RBE

GCAGCCTGAATGGCGAATGGCGATTCCGTTGCAATGGCTGGCGGTAATATTGTTCTGGATATTAC
                                                                          3965
CGTCGGACTTACCGCTTACCGCTAAGGCAACGTTACCGACCGCCATTATAACAAGACCTATAATG
```

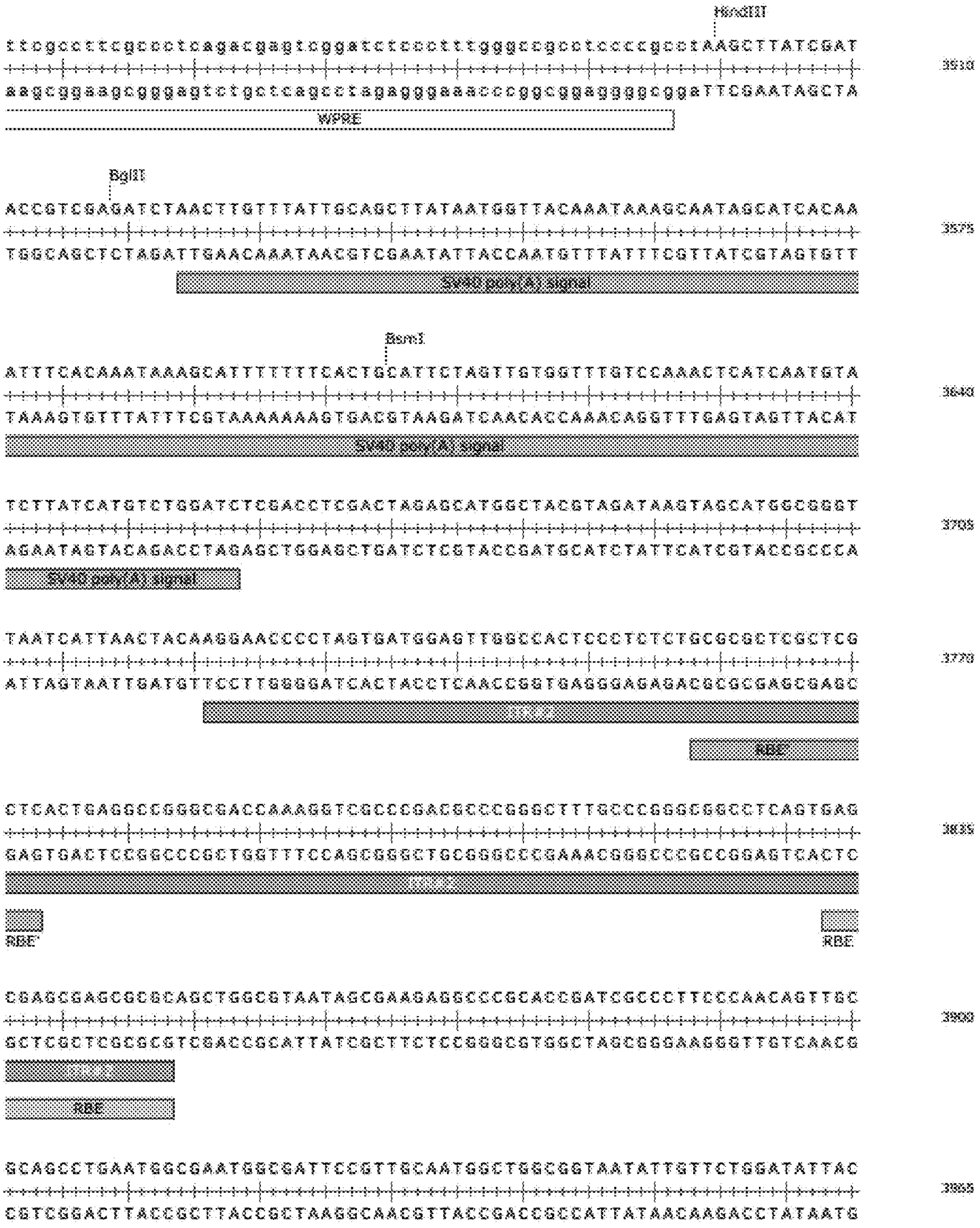

FIG. 9

SEQ ID NO. 1

```
CAGCAAGGCCGATAGTTTGAGTTCTTCTACTCAGGCAAGTGATGTTATTACTAATCAAAGAAGTA
                                                                  4030
GTCGTTCCGGCTATCAAACTCAAGAAGATGAGTCCGTTCACTACAATAATGATTAGTTTCTTCAT

TTGCGACAACGGTTAATTTGCGTGATGGACAGACTCTTTTACTCGGTGGCCTCACTGATTATAAA
                                                                  4095
AACGCTGTTGCCAATTAAACGCACTACCTGTCTGAGAAAATGAGCCACCGGAGTGACTAATATTT

AACACTTCTCAGGATTCTGGCGTACCGTTCCTGTCTAAAATCCCTTTAATCGGCCTCCTGTTTAG
                                                                  4160
TTGTGAAGAGTCCTAAGACCGCATGGCAAGGACAGATTTTAGGGAAATTAGCCGGAGGACAAATC

CTCCCGCTCTGATTCTAACGAGGAAAGCACGTTATACGTGCTCGTCAAAGCAACCATAGTACGCG
                                                                  4225
GAGGGCGAGACTAAGATTGCTCCTTTCGTGCAATATGCACGAGCAGTTTCGTTGGTATCATGCGC
                                                          f1 ori

CCCTGTAGCGGCGCATTAAGCGCGGCGGGTGTGGTGGTTACGCGCAGCGTGACCGCTACACTTGC
                                                                  4290
GGGACATCGCCGCGTAATTCGCGCCGCCCACACCACCAATGCGCGTCGCACTGGCGATGTGAACG
                              f1 ori

CAGCGCCCTAGCGCCCGCTCCTTTCGCTTTCTTCCCTTCCTTTCTCGCCACGTTCGCCGGCTTTC
                                                                  4355
GTCGCGGGATCGCGGGCGAGGAAAGCGAAAGAAGGGAAGGAAAGAGCGGTGCAAGCGGCCGAAAG
                              f1 ori

CCCGTCAAGCTCTAAATCGGGGGCTCCCTTTAGGGTTCCGATTTAGTGCTTTACGGCACCTCGAC
                                                                  4420
GGGCAGTTCGAGATTTAGCCCCCGAGGGAAATCCCAAGGCTAAATCACGAAATGCCGTGGAGCTG
                              f1 ori

CCCAAAAAACTTGATTAGGGTGATGGTTCACGTAGTGGGCCATCGCCCTGATAGACGGTTTTTCG
                                                                  4485
GGGTTTTTTGAACTAATCCCACTACCAAGTGCATCACCCGGTAGCGGGACTATCTGCCAAAAAGC
                              f1 ori

CCCTTTGACGTTGGAGTCCACGTTCTTTAATAGTGGACTCTTGTTCCAAACTGGAACAACACTCA
                                                                  4550
GGGAAACTGCAACCTCAGGTGCAAGAAATTATCACCTGAGAACAAGGTTTGACCTTGTTGTGAGT
                              f1 ori

ACCCTATCTCGGTCTATTCTTTTGATTTATAAGGGATTTTGCCGATTTCGGCCTATTGGTTAAAA
                                                                  4615
TGGGATAGAGCCAGATAAGAAAACTAAATATTCCCTAAAACGGCTAAAGCCGGATAACCAATTTT
                              f1 ori
```

FIG. 10

SEQ ID NO. 1

```
                                                               SwaI
AATGAGCTGATTTAACAAAAATTTAACGCGAATTTTAACAAAATATTAACGTTTACAATTTAAAT   4680
TTACTCGACTAAATTGTTTTTAAATTGCGCTTAAAATTGTTTTATAATTGCAAATGTTAAATTTA
                                f1 ori

ATTTGCTTATACAATCTTCCTGTTTTTGGGGCTTTTCTGATTATCAACCGGGGTACATATGATTG   4745
TAAACGAATATGTTAGAAGGACAAAAACCCCGAAAAGACTAATAGTTGGCCCCATGTATACTAAC

ACATGCTAGTTTTACGATTACCGTTCATCGATTCTCTTGTTTGCTCCAGACTCTCAGGCAATGAC   4810
TGTACGATCAAAATGCTAATGGCAAGTAGCTAAGAGAACAAACGAGGTCTGAGAGTCCGTTACTG

CTGATAGCCTTTGTAGAGACCTCTCAAAAATAGCTACCCTCTCCGGCATGAATTTATCAGCTAGA   4875
GACTATCGGAAACATCTCTGGAGAGTTTTTATCGATGGGAGAGGCCGTACTTAAATAGTCGATCT

ACGGTTGAATATCATATTGATGGTGATTTGACTGTCTCCGGCCTTTCTCACCCGTTTGAATCTTT   4940
TGCCAACTTATAGTATAACTACCACTAAACTGACAGAGGCCGGAAAGAGTGGGCAAACTTAGAAA

ACCTACACATTACTCAGGCATTGCATTTAAAATATATGAGGGTTCTAAAAATTTTTATCCTTGCG   5005
TGGATGTGTAATGAGTCCGTAACGTAAATTTTATATACTCCCAAGATTTTTAAAAATAGGAACGC

TTGAAATAAAGGCTTCTCCCGCAAAAGTATTACAGGGTCATAATGTTTTTGGTACAACCGATTTA   5070
AACTTTATTTCCGAAGAGGGCGTTTTCATAATGTCCCAGTATTACAAAAACCATGTTGGCTAAAT

GCTTTATGCTCTGAGGCTTTATTGCTTAATTTTGCTAATTCTTTGCCTTGCCTGTATGATTTATT   5135
CGAAATACGAGACTCCGAAATAACGAATTAAAACGATTAAGAAACGGAACGGACATACTAAATAA

        EcoRI
GGATGTTGGAATTCCTGATGCGGTATTTTCTCCTTACGCATCTGTGCGGTATTTCACACCGCATA   5200
CCTACAACCTTAAGGACTACGCCATAAAAGAGGAATGCGTAGACACGCCATAAAGTGTGGCGTAT

TGGTGCACTCTCAGTACAATCTGCTCTGATGCCGCATAGTTAAGCCAGCCCCGACACCCGCCAAC   5265
ACCACGTGAGAGTCATGTTAGACGAGACTACGGCGTATCAATTCGGTCGGGGCTGTGGGCGGTTG

ACCCGCTGACGCGCCCTGACGGGCTTGTCTGCTCCCGGCATCCGCTTACAGACAAGCTGTGACCG   5330
TGGGCGACTGCGCGGGACTGCCCGAACAGACGAGGGCCGTAGGCGAATGTCTGTTCGACACTGGC

TCTCCGGGAGCTGCATGTGTCAGAGGTTTTCACCGTCATCACCGAAACGCGCGAGACGAAAGGGC   5395
AGAGGCCCTCGACGTACACAGTCTCCAAAAGTGGCAGTAGTGGCTTTGCGCGCTCTGCTTTCCCG
```

FIG. 11

SEQ ID NO. 1

SEQ ID NO. 1

SEQ ID NO. 1

SEQ ID NO. 1

COMPOSITIONS AND METHODS FOR REGULATING PRODUCTION OF A FUSION PROTEIN AND RIBONUCLEIC ACID

SEQUENCE LISTING

This application contains a Sequence Listing electronically submitted via Patent Center to the United States Patent and Trademark Office as an XML Document file entitled "A8147625US-ST26.xml" created on 2022 Dec. 4 and having a size of 48,355 bytes. The information contained in the Sequence Listing is incorporated by reference herein.

TECHNICAL FIELD

The present disclosure generally relates to compositions and methods for regulating production of a fusion protein and ribonucleic acid (RNA). In particular, the present disclosure relates to compositions and methods for regulating gene expression and, therefore, production of a fusion protein and micro-RNA both of which relate to suppressing immune responses.

BACKGROUND

Bioactive molecules, including enzymes, receptors, receptor agonists and antagonists, are necessary for the homeostatic control of biological systems.

When bioactive molecules are over-expressed, under-expressed or mis-expressed, homeostasis is lost, and disease is often the result.

Known approaches to the treatment of conditions whereby bioactive molecules are over or mis-expressed are the commercially available pharmaceutical products that bind to and block the production or effectiveness of one or more bioactive molecules.

SUMMARY

Some embodiments of the present disclosure relate to one or more compositions that upregulate the production of a belatacept-similar protein (BSP). The BSP has a similar, substantially the same or the same biological function as belatacept when administered to a subject. In some embodiments the compositions comprise a vector of plasmid deoxyribonucleic acid (DNA) that includes an insert sequence of nucleic acids that encode for the production of the BSP and a backbone sequence of nucleic acids that facilitate introduction of the insert sequence into one or more of a subject's cells where the insert sequence is expressed and/or replicated. Expression of the insert sequence by one or more cells of the subject results in an increased production of the BSP by the one or more cells. In some embodiments of the present disclosure, the methods that upregulate the production of BSP relate to methods of manufacturing and administering the composition.

Some embodiments of the present disclosure relate to one or more compositions that upregulate the production of one or more sequences of micro-ribonucleic acid (miRNA). The sequences of miRNA may be complimentary to a sequence of target messenger RNA (mRNA) that encodes for translation of a target biomolecule and the miRNA can cause the target mRNA to be degraded or inactivated, thereby causing a decrease in production of the target biomolecule. In some embodiments of the present disclosure, the target biomolecule is a pro-inflammatory cytokine, such as tumor necrosis factor alpha (TNF-alpha). In some embodiments of the present disclosure, the target biomolecule is an anti-inflammatory cytokine. In some embodiments of the present disclosure the compositions comprise vector DNA that includes one or more an insert sequences of nucleic acids that encode for the production of miRNA and a backbone sequence of nucleic acids that facilitates introduction of the one or more insert sequences into one or more of a subject's cells where it is expressed and/or replicated. Expression of the one or more insert sequences by one or more cells of the subject results in an increased production of the miRNA and, therefore, decreased translation of the target cytokine by one or more of the subject's cells. In some embodiments of the present disclosure, the methods that upregulate the production of the one or more miRNA sequences relate to methods of manufacturing and administering the composition.

Some embodiments of the present disclosure relate to one or more compositions that upregulate the production of both the BSP and miRNA that degrades, or causes degradation of, or inactivates or causes the inactivation of the mRNA of the target biomolecule, such as a cytokine.

Some embodiments of the present disclosure relate to compositions that can be used as a therapy or a treatment for a subject that has a condition whereby the target biomolecule is over or mis-expressed.

Some embodiments of the present disclosure relate to a recombinant plasmid (RP). In some embodiments of the present disclosure, the RP comprises a nucleotide sequence of SEQ ID No. 1. The RP comprises a nucleotide sequence encoding one or more nucleotide sequences encoding for production of the BSP and production of a miRNA sequence that targets mRNA of the target biomolecule; and, an inverted terminal repeat.

Some embodiments of the present disclosure relate to a cassette, which may also be referred to as an insert, for use with an RP, wherein the cassette comprises a nucleotide sequence of SEQ ID No. 1. When the cassette with SEQ ID No. 1 is included in the RP and the RP is administered to a subject, one or more of the subject's cells will upregulate production of the BSP and the miRNA that degrades, or causes degradation of, or inactivates or causes the inactivation of the target mRNA of the target biomolecule. For example, the target biomolecule may be TNF-alpha.

Some embodiments of the present disclosure relate to a method of making a composition/target cell complex. The method comprising a step of administering a RP comprising SEQ ID No. 1 to a target cell for forming the composition/target cell complex, wherein the composition/target cell complex causes the target cell to increase production of BSP and one or more sequences of miRNA that decreases production of a target biomolecule. For example, the target biomolecule may be TNF-alpha.

Some embodiments of the present disclosure relate to a method of making an agent/target cell complex, the method comprising a step of administering a sufficient amount of an agent to a target cell whereby the agent/target cell complex is formed, wherein the agent/target cell complex increases the subject's production of the BSP and the agent/target cell complex also increases the subject's production of one or more sequences of miRNA that decreases the production of a target cytokine.

Some embodiments of the present disclosure relate to a pharmaceutical agent that comprises an agent, a pharmaceutically acceptable carrier and/or an excipient. Administering the pharmaceutical agent to a subject may increase the subject's production of the BSP, one or more sequences of miRNA that decreases the production of a target cytokine or both.

Some embodiments of the present disclosure relate to a method of treating a condition. The method comprises a step of administering to a subject a therapeutically effective amount of an agent that upregulates the subject's production of the BSP, one or more sequences of miRNA that decreases the production of a target cytokine or both.

Some embodiments of the present disclosure relate to a use of an agent for treating a condition, wherein the agent upregulates the subject's production of the BSP, one or more sequences of miRNA that decreases the production of a target cytokine or both.

Embodiments of the present disclosure relate to at least one approach for inducing endogenous production of the BSP and one or more sequences of miRNA that target and silence mRNA of TNF-alpha protein. A first approach utilizes gene vectors containing nucleotide sequences for increasing the endogenous production of BSP and one or more sequences of miRNA that target and silence the mRNA of TNF-alpha, which can be administered to a subject to increase the subject's production of the BSP and one or more sequences of miRNA. Without being bound by any particular theory, embodiments of the present disclosure may be useful for treating conditions wherein the subject's immune system has become dysregulated.

BRIEF DESCRIPTION OF THE DRAWINGS

These and other features of the present disclosure will become more apparent in the following detailed description in which reference is made to the appended drawings.

FIG. 4 is a schematic that represents a third portion of a plasmid vector, according to embodiments of the present disclosure, which is contiguous with the second portion of FIG. 3.

FIG. 8 is a schematic that represents a seventh portion of a plasmid vector, according to embodiments of the present disclosure, which is contiguous with the sixth portion of FIG. 7.

FIG. 9 is a schematic that represents an eighth portion of a plasmid vector, according to embodiments of the present disclosure, which is contiguous with the seventh portion of FIG. 8.

FIG. 10 is a schematic that represents a ninth portion of a plasmid vector, according to embodiments of the present disclosure, which is contiguous with the eighth portion of FIG. 9.

FIG. 11 is a schematic that represents a tenth portion of a plasmid vector, according to embodiments of the present disclosure, which is contiguous with the ninth portion of FIG. 10.

DETAILED DESCRIPTION

Figure 1:
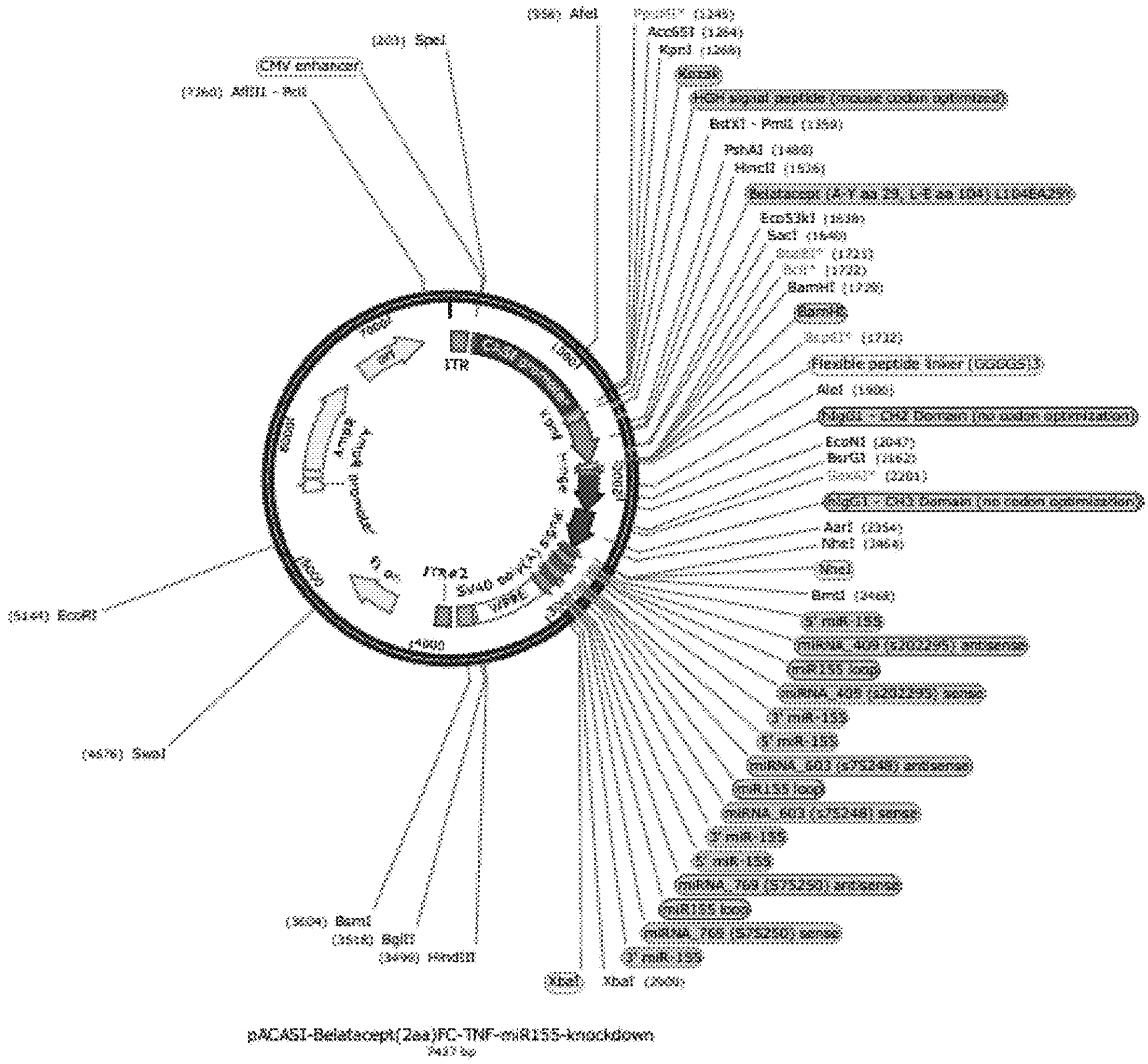
FIG. 1 is a schematic of a vector map that represents a plasmid vector, according to embodiments of the present disclosure.
Figure 2:
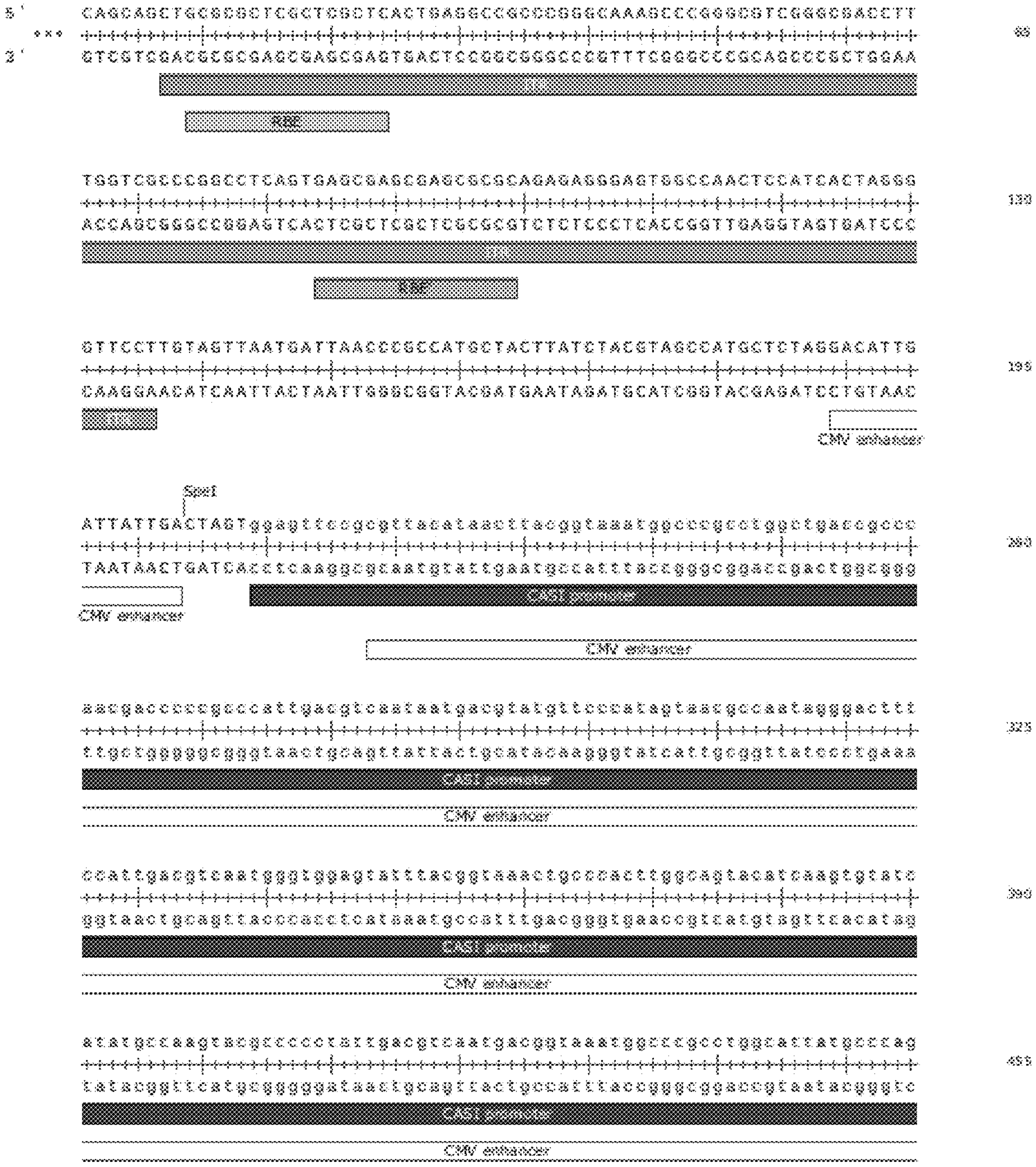
FIG. 2 is a schematic that represents a first portion of a plasmid vector, according to embodiments of the present disclosure.
Figure 3:
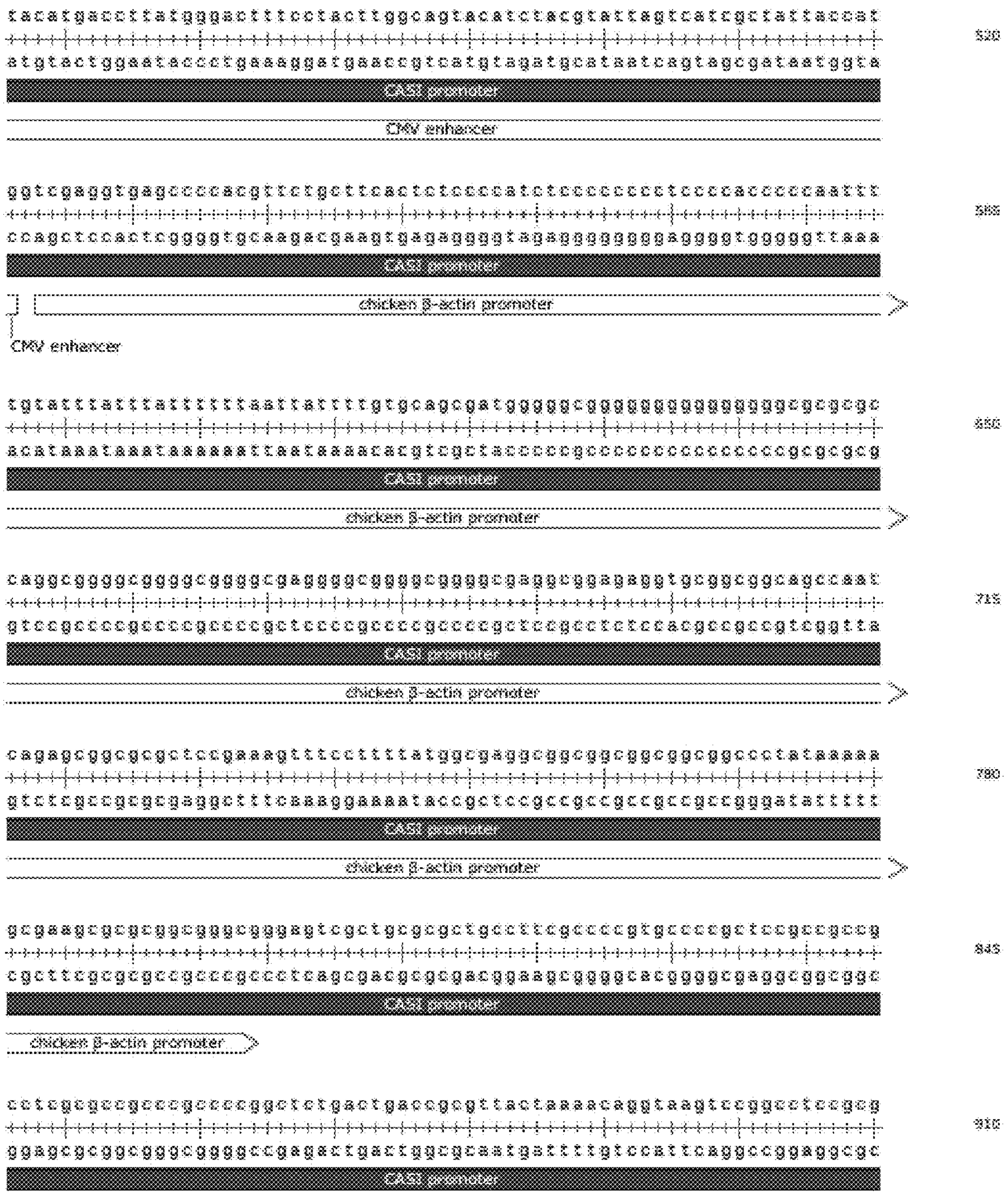
FIG. 3 is a schematic that represents a second portion of a plasmid vector, according to embodiments of the present disclosure, which is contiguous with the first portion of FIG. 2.
Figure 5:
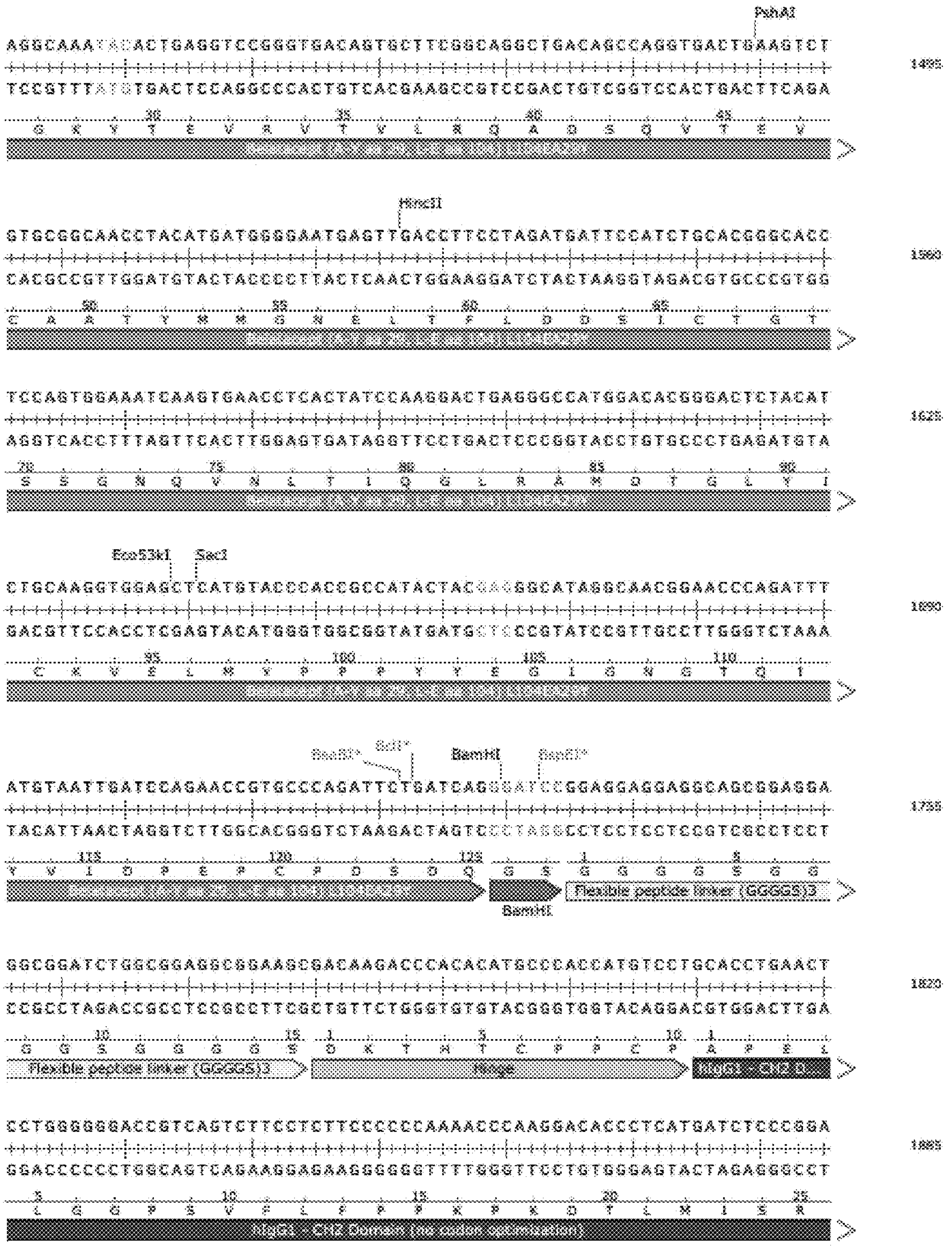
FIG. 5 is a schematic that represents a fourth portion of a plasmid vector, according to embodiments of the present disclosure, which is contiguous with the third portion of FIG. 4.
Figure 6:
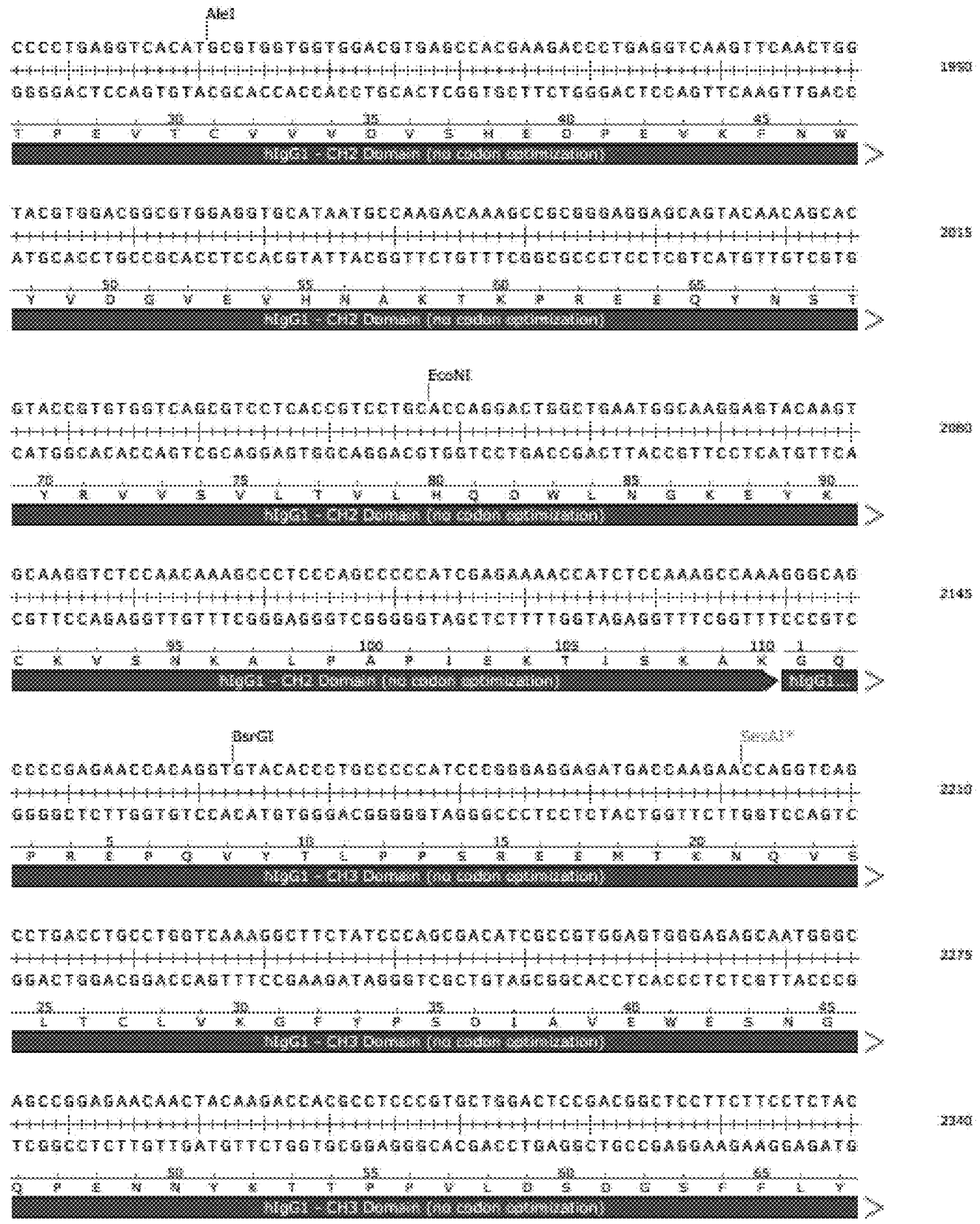
FIG. 6 is a schematic that represents a fifth portion of a plasmid vector, according to embodiments of the present disclosure, which is contiguous with the fourth portion of FIG. 5.
Figure 7:
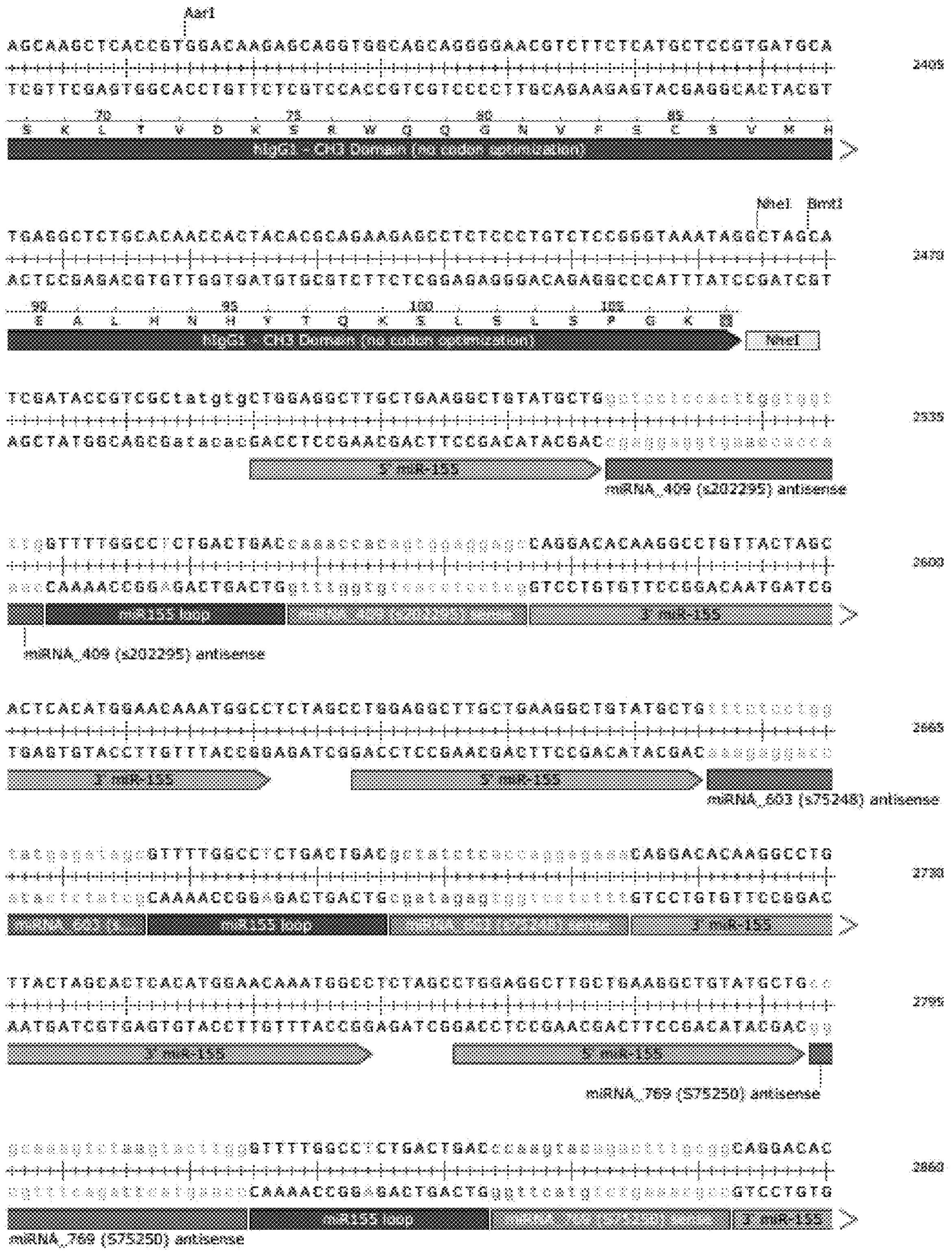
FIG. 7 is a schematic that represents a sixth portion of a plasmid vector, according to embodiments of the present disclosure, which is contiguous with the fifth portion of FIG. 6.
Figure 12:
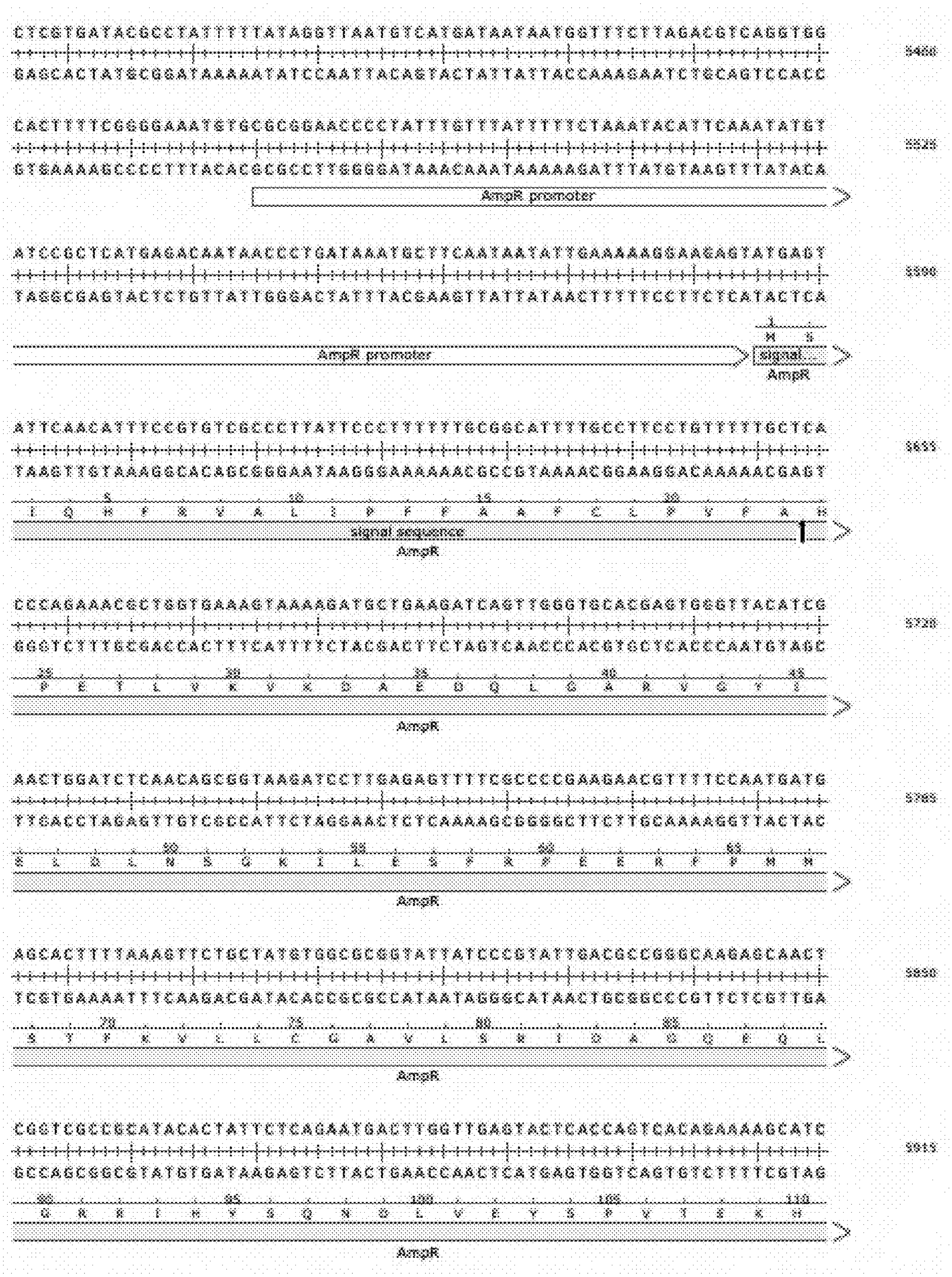
FIG. 12 is a schematic that represents an eleventh portion of a plasmid vector, according to embodiments of the present disclosure, which is contiguous with the tenth portion of FIG. 11.
Figure 13:
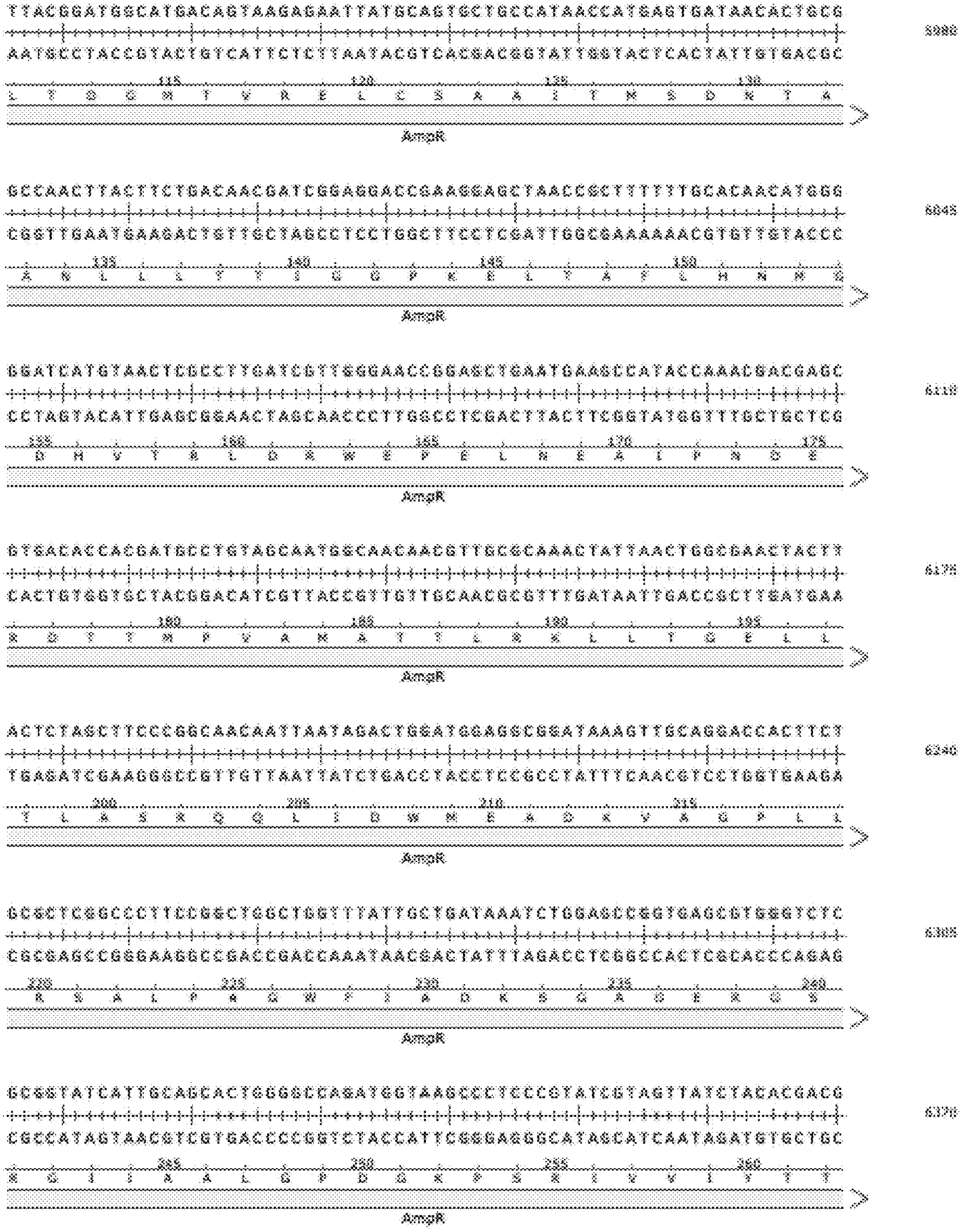
FIG. 13 is a schematic that represents a twelfth portion of a plasmid vector, according to embodiments of the present disclosure, which is contiguous with the eleventh portion of FIG. 12.
Figure 14:
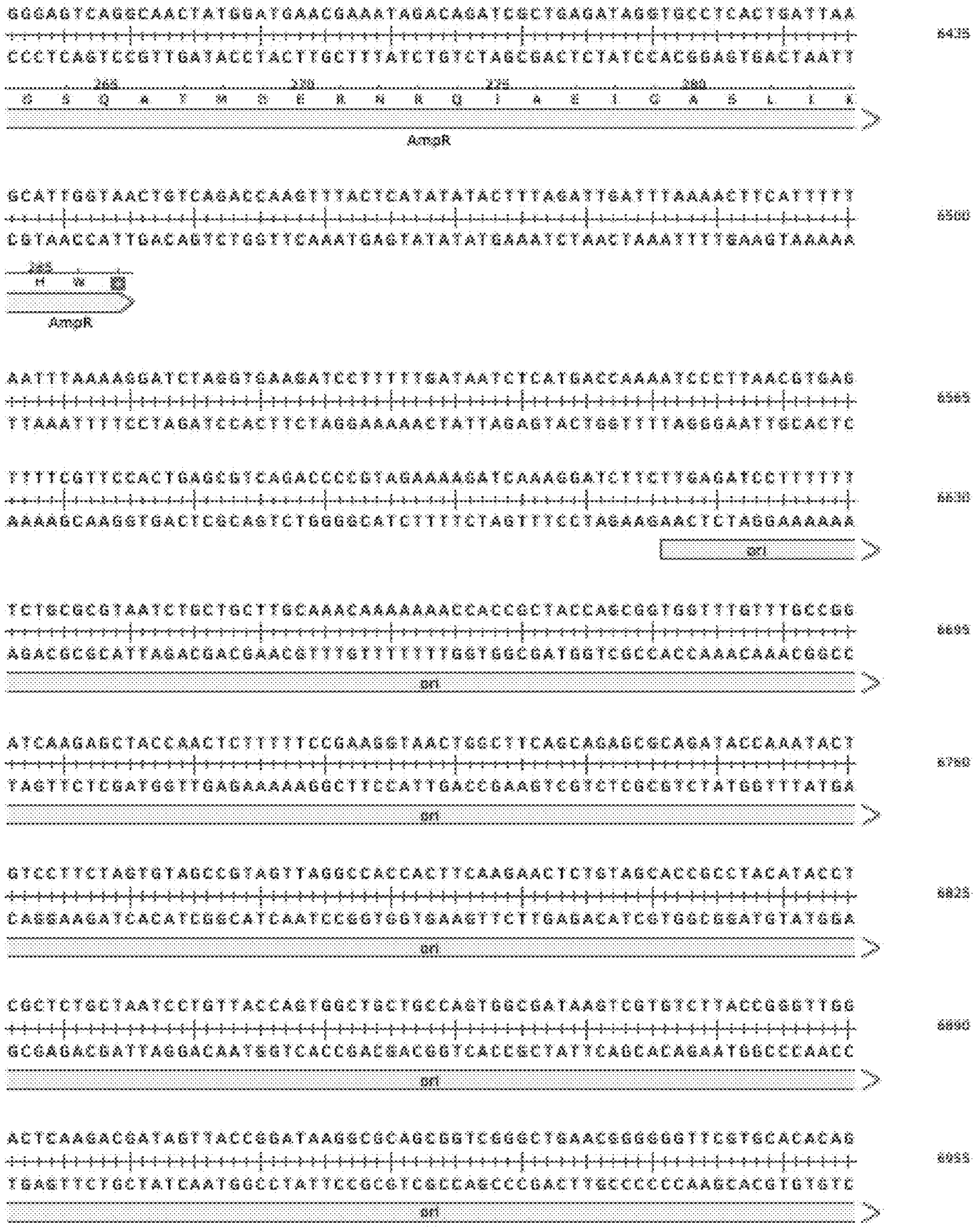
FIG. 14 is a schematic that represents a thirteenth portion of a plasmid vector, according to embodiments of the present disclosure, which is contiguous with the twelfth portion of FIG. 13.
Figure 15:
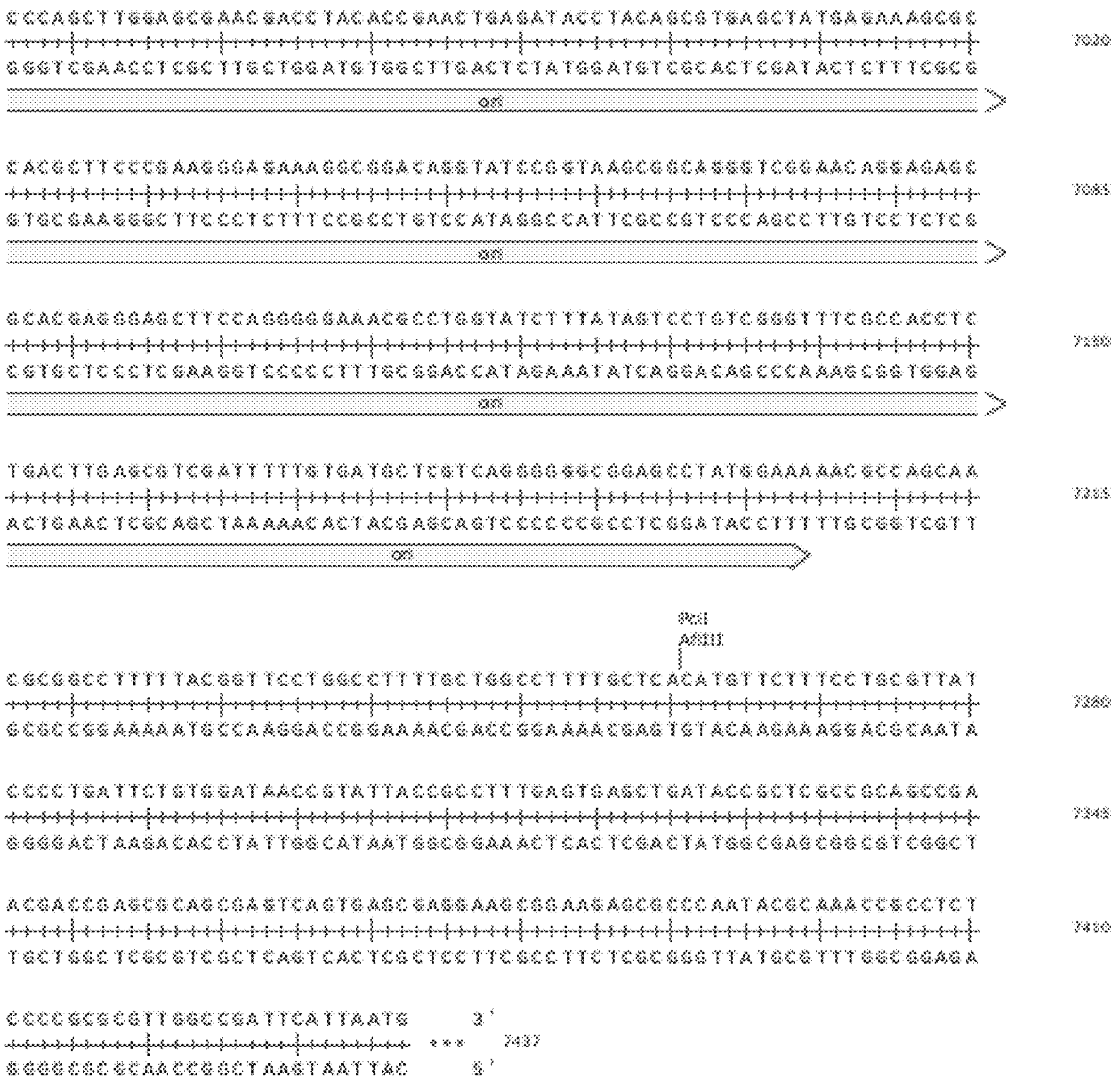
FIG. 15 is a schematic that represents a fourteenth portion of a plasmid vector, according to embodiments of the present disclosure, which is contiguous with the thirteenth portion of FIG. 14.
Figure 16:
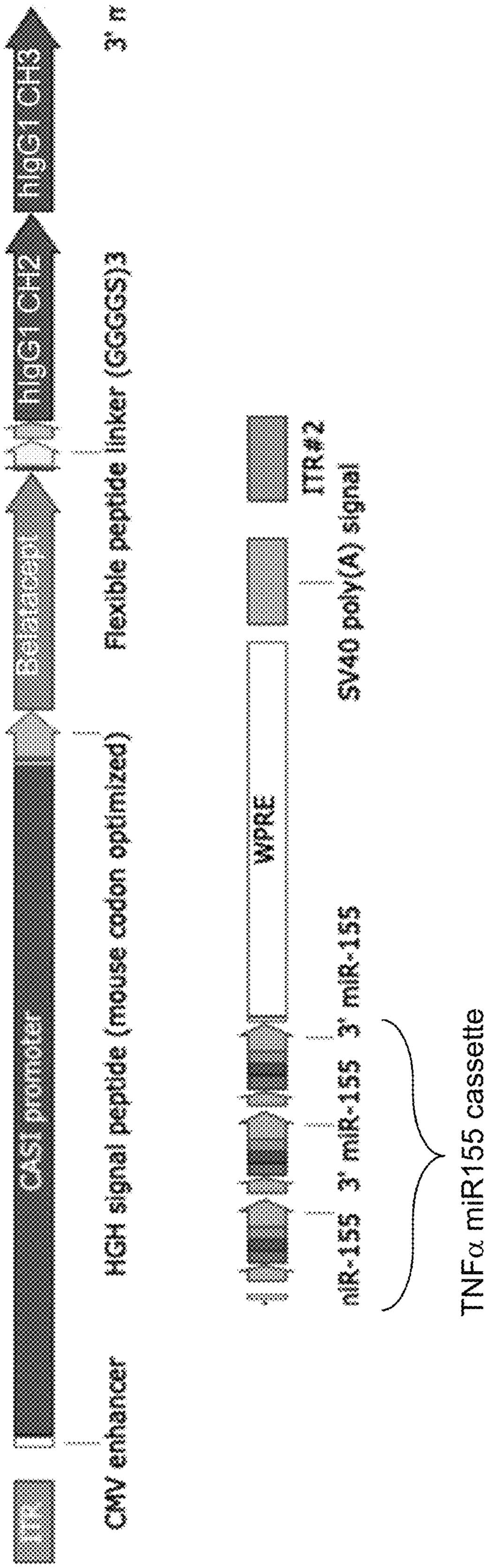
FIG. 16 is a schematic of an adeno-associated viral genome, according to embodiments of the present disclosure.

Unless defined otherwise, all technical and scientific terms used herein have the meanings that would be commonly understood by one of skill in the art in the context of the present description. Although any methods and materials similar or equivalent to those described herein can also be used in the practice or testing of the present disclosure, the preferred methods and materials are now described. All publications mentioned herein are incorporated herein by reference to disclose and describe the methods and/or materials in connection with which the publications are cited.

As used herein, the singular forms "a", "an", and "the" include plural references unless the context clearly dictates otherwise. For example, reference to "an agent" includes one or more agents and reference to "a subject" or "the subject" includes one or more subjects.

As used herein, the terms "about" or "approximately" refer to within about 25%, preferably within about 20%, preferably within about 15%, preferably within about 10%, preferably within about 5% of a given value or range. It is understood that such a variation is always included in any given value provided herein, whether or not it is specifically referred to.

As used herein, the term "activity" is used interchangeably with the term "functionality" and both terms refer to the physiologic action of biomolecule.

As used herein, the term "agent" refers to a substance that, when administered to a subject, causes one or more chemical reactions and/or one or more physical reactions and/or or one or more physiological reactions and/or one or more immunological reactions in the subject. In some embodiments of the present disclosure, the agent is a plasmid vector. Agent may be used interchangeably with the terms "compound" and/or "composition".

As used herein, the term "ameliorate" refers to improve and/or to make better and/or to make more satisfactory.

As used herein, the term "biomolecule" refers to a carbohydrate, a protein, an amino acid sequence, a nucleic acid, a lipid, a primary metabolite, a secondary metabolite or another metabolite that is found within a subject. A biomolecule may be endogenous or exogenous to a subject.

As used herein, the term "cell" refers to a single cell as well as a plurality of cells or a population of the same cell type or different cell types. Administering an agent to a cell includes in vivo, in vitro and ex vivo administrations and/or combinations thereof.

As used herein, the term "complex" refers to an association, either direct or indirect, between one or more particles of an agent and one or more target cells. This association results in a change in the metabolism of the target cell. As used herein, the phrase "change in metabolism" refers to an increase or a decrease in the one or more target cells' production of deoxyribonucleic acid (DNA), ribonucleic acid (RNA), one or more proteins, and/or any post-translational modifications of one or more proteins.

As used herein, the terms "dysregulation" and "dysregulated" refer to situations or conditions wherein homeostatic control systems have been disturbed and/or compromised so that one or more metabolic, physiologic and/or biochemical systems within a subject operate partially or entirely without said homeostatic control systems.

As used herein, the term "endogenous" refers to the production and/or modification of a molecule that originates within a subject.

As used herein, the term "exogenous" refers to a molecule that is within a subject but that did not originate within the subject.

As used herein, the terms "inhibit", "inhibiting", and "inhibition" refer to a decrease in activity, response, or other biological parameter of a biologic process, disease, disorder or symptom thereof. This can include but is not limited to the complete ablation of the activity, response, condition, or disease. This may also include, for example, a 10% reduction in the activity, response, condition, or disease as compared to the native or control level. Thus, the reduction can be a 10%, 20%, 30%, 40%, 50%, 60%, 70%, 80%, 90%, 100%, or any amount of reduction in between the specifically recited percentages, as compared to native or control levels.

As used herein, the phrases "prevention of" and "preventing" refer to avoiding the onset or progression of a disease, disorder, or a symptom thereof.

As used herein, the terms "production", "producing" and "produce" refer to the synthesis and/or replication of DNA, the transcription of one or more sequences of RNA, the translation of one or more amino acid sequences, the post-translational modifications of an amino acid sequence, and/or the production of one or more regulatory molecules that can influence the production and/or functionality of an effector molecule or an effector cell. For clarity, "production" is also be used herein to refer to the functionality of a regulatory molecule, unless the context reasonably indicates otherwise.

As used herein, the terms "promote", "promotion", and "promoting" refer to an increase in an activity, response, condition, disease process, or other biological parameter. This can include, but is not limited to, the initiation of the activity, response, condition, or disease process. This may also include, for example, a 10% increase in the activity, response, condition, or disease as compared to the native or control level. Thus, the increase in an activity, response, condition, disease, or other biological parameter can be 10%, 20%, 30%, 40%, 50%, 60%, 70%, 80%, 90%, 100%, or more, including any amount of increase in between the specifically recited percentages, as compared to native or control levels.

As used herein, the term "subject" refers to any therapeutic target that receives the agent. The subject can be a vertebrate, for example, a mammal including a human. The term "subject" does not denote a particular age or sex. The term "subject" also refers to one or more cells of an organism, an in vitro culture of one or more tissue types, an in vitro culture of one or more cell types, ex vivo preparations, and/or a sample of biological materials such as tissue and/or biological fluids.

As used herein, the term "target cell" refers to one or more cells and/or cell types that are deleteriously affected, either directly or indirectly, by a dysregulated immune system and/or a disease process. The term "target cell" also refers to cells that are not deleteriously affected but that are the cells in which it is desired that the agent interacts.

As used herein, the term "therapeutically effective amount" refers to the amount of the agent used that is of sufficient quantity to ameliorate, treat and/or inhibit one or more of a disease, disorder or a symptom thereof. The "therapeutically effective amount" will vary depending on the agent used, the route of administration of the agent and the severity of the disease, disorder or symptom thereof. The subject's age, weight and genetic make-up may also influence the amount of the agent that will be a therapeutically effective amount.

As used herein, the terms "treat", "treatment" and "treating" refer to obtaining a desired pharmacologic and/or physiologic effect. The effect may be prophylactic in terms of completely or partially preventing an occurrence of a disease, disorder or symptom thereof and/or the effect may be therapeutic in providing a partial or complete amelioration or inhibition of a disease, disorder, or symptom thereof. Additionally, the term "treatment" refers to any treatment of a disease, disorder, or symptom thereof in a subject and includes: (a) preventing the disease from occurring in a subject which may be predisposed to the disease but has not yet been diagnosed as having it; (b) inhibiting the disease, i.e., arresting its development; and (c) ameliorating the disease.

As used herein, the terms "unit dosage form" and "unit dose" refer to a physically discrete unit that is suitable as a unitary dose for patients. Each unit contains a predetermined quantity of the agent and optionally, one or more suitable pharmaceutically acceptable carriers, one or more excipients, one or more additional active ingredients, or combinations thereof. The amount of agent within each unit is a therapeutically effective amount.

Where a range of values is provided herein, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges, and are also, encompassed within the disclosure, subject to any specifically excluded limit in the stated range. Where the stated range includes one or both of the limits, ranges excluding either or both of those included limits are also included in the disclosure.

Some embodiments of the present disclosure relate to a recombinant plasmid (RP) for introducing genetic material, such as one or more nucleotide sequences, into a target cell for reproduction or transcription of an insert that comprises one or more nucleotide sequences that are carried within the RP. In some embodiments of the present disclosure, the RP is delivered by a viral vector. In some embodiments of the present disclosure, the vector is an adeno-associated virus vector.

In some embodiments of the present disclosure, the insert comprises one or more nucleotide sequences that encode for production of at least a belatacept similar protein (BSP).

The BSP has physiologic/biologic equivalence to belatacept, meaning the BSP will have substantially the same effect on the subject or target cell as a similar dose of belatacept will. Belatacept is a known immunosuppressant that is used to reduce rejection in recipients of organ transplants. Similar to belatacept, BSP is a fusion protein that combines an Fc portion of a human immunoglobulin IgG1 with an extracellular portion of cytotoxic T-lymphocyte-associated protein 4 (CTLA-4). Belatacept can interfere with binding of antigen presenting cells and, therefore, belatacept can prevent activation of T-cells. As such, the BSP may also prevent activation of T-cells.

In some embodiments of the present disclosure, the insert comprises one or more nucleotide sequences that encode for production of at least one sequence of miRNA that decreases the production of target cytokine proteins. The miRNA may, directly or indirectly, bind to and degrade the target mRNA or otherwise inactivate the target mRNA so that less or none of the target-cytokine protein is produced.

In some embodiments of the present disclosure, the target cytokine is a pro-inflammatory cytokine, meaning it has the physiologic effect of increasing inflammatory processes in the subject. In some embodiments of the present disclosure, the target cytokine is TNF-alpha. In some embodiments of the present disclosure, the target cytokine is an anti-inflammatory cytokine.

In some embodiments of the present disclosure, the insert comprises two or more nucleotide sequences that each encode one or more miRNA sequences that may be complimentary to and degrade, or cause degradation of, mRNA of the target cytokine. In some embodiments of the present disclosure the insert comprises three nucleotide sequences that each encode an miRNA sequence that may be complimentary to and degrade, or causes degradation of, or inactivates or causes inactivation of mRNA of the target cytokine.

In some embodiments of the present disclosure, the insert comprises one or more nucleotide sequences that encode for production of the BSP and one or more nucleotide sequences that each encode for an miRNA sequence that is complimentary to and degrades, or causes degradation of, or inactivates or causes inactivation of mRNA of the target cytokine. In some embodiments of the present disclosure, the insert comprises two nucleotide sequences that each encode for miRNA that may be complimentary to and degrade, or causes degradation of, or inactivate, or causes inactivation of mRNA of the target cytokine. In some embodiments of the present disclosure, the insert comprises three nucleotide sequences that each encode for miRNA that may be complimentary to and degrade, or causes degradation of, or inactivate, or causes inactivation of mRNA of the target cytokine. In some embodiments of the present disclosure, the insert comprises more than three nucleotide sequences that each encode for miRNA that may be complimentary to and degrade, or causes degradation of, or inactivate, or causes inactivation of mRNA of the target cytokine.

The present disclosure relates to one or more agents, therapies, treatments, and methods of use of the agents and/or therapies and/or treatments for initiating or upregulating production of the BSP while downregulating production and/or functionality of the target cytokine. Some embodiments of the present disclosure relate to methods for making a complex between at least one particle of an agent and at least one target cell of a subject for initiating or increasing production of the BSP and for downregulating the subject's production and/or functionality of the target cytokine. Embodiments of the present disclosure can be used as a therapy or a treatment for a subject that has a condition whereby the subject's immune system is, or is likely to become, dysregulated.

In some embodiments of the present disclosure, the agent can be administered to the subject by an intravenous route, an intramuscular route, an intraperitoneal route, an intrathecal route, an intravesical route, a topical route, an intranasal route, a transmucosal route, a pulmonary route, and combinations thereof.

In some embodiments of the present disclosure, the agent can be administered to the subject by pipetting a dose of the agent into an in vitro cell culture, perfusing or immersing an ex vivo cell or tissue preparation with a solution that comprises the agent, mixing a biological fluid sample with a solution or substrate that comprises the agent, or combinations thereof.

Some embodiments of the present disclosure relate to an agent that can be administered to a subject with a condition that results from, directly or indirectly, a dysregulated immune system. When a therapeutically effective amount of the agent is administered to the subject, the subject may change production and/or functionality of one or more immune system molecules. For example, the subject may decrease production and/or functionality of one or more immune system signaling molecules and/or one or more immune system effector molecules by changing the production of one or more sequences of DNA, one or more sequences of RNA and/or one or more proteins and/or one or more regulatory molecules that regulate the levels and/or functionality of the subject's immune system signaling molecules and/or immune system effector molecules.

In some embodiments of the present disclosure, the subject may respond to receiving the therapeutic amount of the agent by changing production and/or functionality of one or more intermediary molecules by changing production of one or more DNA sequences, one or more RNA sequences, and/or one or more proteins that regulate the levels and/or functionality of the one or more intermediary molecules. The one or more intermediary molecules regulate the subject's levels and/or functionality of the one or more immune system signaling molecules and/or the one or more immune system effector molecules.

In some embodiments of the present disclosure, administering a therapeutic amount of the agent to a subject upregulates the production, functionality or both of the BSP and one or more sequences of miRNA that each target the mRNA of one or more target cytokines. Examples of the target cytokine include one or more pro-inflammatory cytokines, one or more anti-inflammatory cytokines or combinations thereof. In some embodiments of the present disclosure, there are one, two three, four, five, six, seven, eight, nine or ten miRNA sequences that each are complimentary to and degrade, or cause degradation of, one cytokine, such as TNF-alpha. In some embodiments of the present disclosure, the agent may comprise multiple copies of the same nucleotide sequence of miRNA.

In some embodiments of the present disclosure, the composition is an RP that may be used for gene therapy. The gene therapy is useful for increasing the subject's endogenous production of the BSP and one or more sequences of miRNA that target the mRNA of a target cytokine. For example, the RP can contain one or more nucleotide sequences that that cause increased production of the BSP and one or more nucleotide sequences that cause an increased production of one or more miRNA sequences that that each are complimentary to and degrade, or cause degradation of, or inactivate, or cause inactivation of one cytokine, such as TNF-alpha.

In some embodiments of the present disclosure, the RP can be carried by a vector—also referred to as a delivery vehicle—that is a virus used for gene therapy that can be enveloped or not (undeveloped), replication effective or not (replicative ineffective), or combinations thereof. In some embodiments of the present disclosure, the vector is a virus that is not enveloped and replication ineffective. In some embodiments of the present disclosure, the vector is a virus of the Paroviridae family. In some embodiments of the present disclosure, the vector is a virus of the genus Dependoparvaovirus. In some embodiments of the present disclosure, the vector is an adeno-associated virus (AAV). In some embodiments of the present disclosure, the vector is a recombinant AAV. In some embodiments of the present disclosure, the vector is a recombinant AAV6.2FF.

The embodiments of the present disclosure also relate to administering a therapeutically effective amount of the agent. In some embodiments of the present disclosure, the therapeutically effective amount of the agent that is administered to a patient is between about 10 and about $1\times10^{16}$ $TCID_{50}$/kg (50% tissue culture infective dose per kilogram of the patient's body weight). In some embodiments of the present disclosure, the therapeutically effective amount of the agent that is administered to the patient is about $1\times10^{13}$ $TCID_{50}$/kg. In some embodiments of the present disclosure, the therapeutically effective amount of the agent that is administered to a patient is measured in TPC/kg (total particle count of the agent per kilogram of the patient's body weight). In some embodiments the therapeutically effective amount of the agent is between about 10 and about $1\times10^{16}$ TCP/kg.

Some embodiments of the present disclosure relate to an adenovirus associated virus (AAV) genome comprising an RP that when operable inside a target cell will cause the target cell to produce both the BSP and a miRNA sequence that downregulates production of TNF-α. The AAV vector is comprised of AAV2 inverted terminal repeats (ITRs), a composite CASI promoter, the coding sequence for the BSP with a human growth hormone (HGH) signal peptide followed by a miR155 microRNA cassette containing three different siRNAs targeting murine TNF-α, a woodchuck hepatitis virus post-transcriptional regulatory element (WPRE), and an SV40 polyA signal.

```
SEQ ID No. 1 (whole RP):
cagcagctgc gcgctcgctc gctcactgag gccgcccggg caaagcccgg gcgtcgggcg      60
acctttggtc gcccggcctc agtgagcgag cgagcgcgca gagagggagt ggccaactcc     120
atcactaggg gttccttgta gttaatgatt aacccgccat gctacttatc tacgtagcca     180
tgctctagga cattgattat tgactagtgg agttccgcgt tacataactt acggtaaatg     240
gcccgcctgg ctgaccgccc aacgaccccc gcccattgac gtcaataatg acgtatgttc     300
ccatagtaac gccaataggg actttccatt gacgtcaatg ggtggagtat ttacggtaaa     360
ctgcccactt ggcagtacat caagtgtatc atatgccaag tacgccccct attgacgtca     420
atgacggtaa atggcccgcc tggcattatg cccagtacat gaccttatgg gactttccta     480
cttggcagta catctacgta ttagtcatcg ctattaccat ggtcgaggtg agccccacgt     540
tctgcttcac tctccccatc tcccccccct ccccaccccc aattttgtat ttatttattt     600
tttaattatt ttgtgcagcg atgggggcgg gggggggggg gggcgcgcgc caggcggggc     660
ggggcggggc gaggggcggg gcggggcgag gcggagaggt gcggcggcag ccaatcagag     720
cggcgcgctc cgaaagtttc cttttatggc gaggcggcgg cggcggcggc cctataaaaa     780
gcgaagcgcg cggcgggcgg gagtcgctgc gcgctgcctt cgccccgtgc cccgctccgc     840
cgccgcctcg cgccgcccgc cccggctctg actgaccgcg ttactaaaac aggtaagtcc     900
ggcctccgcg ccgggttttg gcgcctcccg cgggcgcccc cctcctcacg gcgagcgctg     960
ccacgtcaga cgaagggcgc agcgagcgtc ctgatccttc cgcccggacg ctcaggacag    1020
cggcccgctg ctcataagac tcggccttag aaccccagta tcagcagaag gacattttag    1080
gacgggactt gggtgactct agggcactgg ttttctttcc agagagcgga acaggcgagg    1140
aaaagtagtc ccttctcggc gattctgcgg agggatctcc gtggggcggt gaacgccgat    1200
gatgcctcta ctaaccatgt tcatgttttc tttttttttc tacaggtcct gggtgacgaa    1260
```

-continued

```
cagggtaccg ccaccatggc caccggctct cgcacaagcc tgctgctggc tttcggactg      1320
ctgtgcctgc cttggctcca ggagggctcc gccatgcacg tggcccagcc tgctgtggta      1380
ctggccagca gccgaggcat cgccagcttt gtgtgtgagt atgcatctcc aggcaaatac      1440
actgaggtcc gggtgacagt gcttcggcag gctgacagcc aggtgactga agtctgtgcg      1500
gcaacctaca tgatggggaa tgagttgacc ttcctagatg attccatctg cacgggcacc      1560
tccagtggaa atcaagtgaa cctcactatc caaggactga gggccatgga cacgggactc      1620
tacatctgca aggtggagct catgtaccca ccgccatact acgagggcat aggcaacgga      1680
acccagattt atgtaattga tccagaaccg tgcccagatt ctgatcaggg atccggagga      1740
ggaggcagcg gaggaggcgg atctggcgga ggcggaagcg acaagaccca cacatgccca      1800
ccatgtcctg cacctgaact cctgggggga ccgtcagtct tcctcttccc cccaaaaccc      1860
aaggacaccc tcatgatctc ccggacccct gaggtcacat gcgtggtggt ggacgtgagc      1920
cacgaagacc ctgaggtcaa gttcaactgg tacgtggacg gcgtggaggt gcataatgcc      1980
aagacaaagc cgcgggagga gcagtacaac agcacgtacc gtgtggtcag cgtcctcacc      2040
gtcctgcacc aggactggct gaatggcaag gagtacaagt gcaaggtctc caacaaagcc      2100
ctcccagccc ccatcgagaa aaccatctcc aaagccaaag ggcagccccg agaaccacag      2160
gtgtacaccc tgcccccatc ccgggaggag atgaccaaga accaggtcag cctgacctgc      2220
ctggtcaaag gcttctatcc cagcgacatc gccgtggagt gggagagcaa tgggcagccg      2280
gagaacaact acaagaccac gcctcccgtg ctggactccg acggctcctt cttcctctac      2340
agcaagctca ccgtggacaa gagcaggtgg cagcagggga acgtcttctc atgctccgtg      2400
atgcatgagg ctctgcacaa ccactacacg cagaagagcc tctccctgtc tccgggtaaa      2460
taggctagca tcgataccgt cgctatgtgc tggaggcttg ctgaaggctg tatgctggct      2520
cctccacttg gtggtttggt tttggcctct gactgaccaa accacagtgg aggagccagg      2580
acacaaggcc tgttactagc actcacatgg aacaaatggc ctctagcctg gaggcttgct      2640
gaaggctgta tgctgtttct cctggtatga gatagcgttt tggcctctga ctgacgctat      2700
ctcaccagga gaaacaggac acaaggcctg ttactagcac tcacatggaa caaatggcct      2760
ctagcctgga ggcttgctga aggctgtatg ctgccgcaaa gtctaagtac ttgggttttg      2820
gcctctgact gacccaagta cagactttgc ggcaggacac aaggcctgtt actagcactc      2880
acatggaaca aatggcctct ctagaataat caacctctgg attacaaaat ttgtgaaaga      2940
ttgactggta ttcttaacta tgttgctcct tttacgctat gtggatacgc tgctttaatg      3000
cctttgtatc atgctattgc ttcccgtatg gctttcattt tctcctcctt gtataaatcc      3060
tggttgctgt ctctttatga ggagttgtgg cccgttgtca ggcaacgtgg cgtggtgtgc      3120
actgtgtttg ctgacgcaac ccccactggt tggggcattg ccaccacctg tcagctcctt      3180
tccgggactt tcgctttccc cctccctatt gccacggcgg aactcatcgc cgcctgcctt      3240
gcccgctgct ggacaggggc tcggctgttg ggcactgaca attccgtggt gttgtcgggg      3300
aaatcatcgt cctttccttg gctgctcgcc tgtgttgcca cctggattct gcgcgggacg      3360
tccttctgct acgtcccttc ggccctcaat ccagcggacc ttccttcccg cggcctgctg      3420
ccggctctgc ggcctcttcc gcgtcttcgc cttcgccctc agacgagtcg gatctccctt      3480
tgggccgcct ccccgcctaa gcttatcgat accgtcgaga tctaacttgt ttattgcagc      3540
ttataatggt tacaaataaa gcaatagcat cacaaatttc acaaataaag catttttttc      3600
actgcattct agttgtggtt tgtccaaact catcaatgta tcttatcatg tctggatctc      3660
gacctcgact agagcatggc tacgtagata agtagcatgg cgggttaatc attaactaca      3720
```

-continued

```
aggaacccct agtgatggag ttggccactc cctctctgcg cgctcgctcg ctcactgagg     3780
ccgggcgacc aaaggtcgcc cgacgcccgg gctttgcccg ggcggcctca gtgagcgagc     3840
gagcgcgcag ctggcgtaat agcgaagagg cccgcaccga tcgcccttcc caacagttgc     3900
gcagcctgaa tggcgaatgg cgattccgtt gcaatggctg gcggtaatat tgttctggat     3960
attaccagca aggccgatag tttgagttct tctactcagg caagtgatgt tattactaat     4020
caaagaagta ttgcgacaac ggttaatttg cgtgatggac agactctttt actcggtggc     4080
ctcactgatt ataaaaacac ttctcaggat tctggcgtac cgttcctgtc taaaatccct     4140
ttaatcggcc tcctgtttag ctcccgctct gattctaacg aggaaagcac gttatacgtg     4200
ctcgtcaaag caaccatagt acgcgccctg tagcggcgca ttaagcgcgg cgggtgtggt     4260
ggttacgcgc agcgtgaccg ctacacttgc cagcgcccta gcgcccgctc ctttcgcttt     4320
cttcccttcc tttctcgcca cgttcgccgg ctttccccgt caagctctaa atcgggggct     4380
ccctttaggg ttccgattta gtgctttacg gcacctcgac cccaaaaaac ttgattaggg     4440
tgatggttca cgtagtgggc catcgccctg atagacggtt tttcgccctt tgacgttgga     4500
gtccacgttc tttaatagtg gactcttgtt ccaaactgga acaacactca accctatctc     4560
ggtctattct tttgatttat aagggatttt gccgatttcg gcctattggt taaaaaatga     4620
gctgatttaa caaaaattta acgcgaattt taacaaaata ttaacgttta caatttaaat     4680
atttgcttat acaatcttcc tgtttttggg gcttttctga ttatcaaccg gggtacatat     4740
gattgacatg ctagttttac gattaccgtt catcgattct cttgtttgct ccagactctc     4800
aggcaatgac ctgatagcct ttgtagagac ctctcaaaaa tagctaccct ctccggcatg     4860
aatttatcag ctagaacggt tgaatatcat attgatggtg atttgactgt ctccggcctt     4920
tctcacccgt ttgaatcttt acctacacat tactcaggca ttgcatttaa aatatatgag     4980
ggttctaaaa atttttatcc ttgcgttgaa ataaaggctt ctcccgcaaa agtattacag     5040
ggtcataatg tttttggtac aaccgattta gctttatgct ctgaggcttt attgcttaat     5100
tttgctaatt ctttgccttg cctgtatgat ttattggatg ttggaattcc tgatgcggta     5160
ttttctcctt acgcatctgt gcggtatttc acaccgcata tggtgcactc tcagtacaat     5220
ctgctctgat gccgcatagt taagccagcc ccgacacccg ccaacacccg ctgacgcgcc     5280
ctgacgggct tgtctgctcc cggcatccgc ttacagacaa gctgtgaccg tctccgggag     5340
ctgcatgtgt cagaggtttt caccgtcatc accgaaacgc gcgagacgaa agggcctcgt     5400
gatacgccta tttttatagg ttaatgtcat gataataatg gtttcttaga cgtcaggtgg     5460
cacttttcgg ggaaatgtgc gcggaacccc tatttgttta tttttctaaa tacattcaaa     5520
tatgtatccg ctcatgagac aataaccctg ataaatgctt caataatatt gaaaaaggaa     5580
gagtatgagt attcaacatt tccgtgtcgc ccttattccc ttttttgcgg cattttgcct     5640
tcctgttttt gctcacccag aaacgctggt gaaagtaaaa gatgctgaag atcagttggg     5700
tgcacgagtg ggttacatcg aactggatct caacagcggt aagatccttg agagttttcg     5760
ccccgaagaa cgttttccaa tgatgagcac ttttaaagtt ctgctatgtg gcgcggtatt     5820
atcccgtatt gacgccgggc aagagcaact cggtcgccgc atacactatt ctcagaatga     5880
cttggttgag tactcaccag tcacagaaaa gcatcttacg gatggcatga cagtaagaga     5940
attatgcagt gctgccataa ccatgagtga taacactgcg gccaacttac ttctgacaac     6000
gatcggagga ccgaaggagc taaccgcttt tttgcacaac atgggggatc atgtaactcg     6060
ccttgatcgt tgggaaccgg agctgaatga agccatacca aacgacgagc gtgacaccac     6120
```

-continued

```
gatgcctgta gcaatggcaa caacgttgcg caaactatta actggcgaac tacttactct      6180
agcttcccgg caacaattaa tagactggat ggaggcggat aaagttgcag gaccacttct      6240
gcgctcggcc cttccggctg gctggtttat tgctgataaa tctggagccg gtgagcgtgg      6300
gtctcgcggt atcattgcag cactggggcc agatggtaag ccctcccgta tcgtagttat      6360
ctacacgacg gggagtcagg caactatgga tgaacgaaat agacagatcg ctgagatagg      6420
tgcctcactg attaagcatt ggtaactgtc agaccaagtt tactcatata tactttagat      6480
tgatttaaaa cttcattttt aatttaaaag gatctaggtg aagatccttt ttgataatct      6540
catgaccaaa atcccttaac gtgagttttc gttccactga gcgtcagacc ccgtagaaaa      6600
gatcaaagga tcttcttgag atcctttttt tctgcgcgta atctgctgct tgcaaacaaa      6660
aaaaccaccg ctaccagcgg tggtttgttt gccggatcaa gagctaccaa ctctttttcc      6720
gaaggtaact ggcttcagca gagcgcagat accaaatact gtccttctag tgtagccgta      6780
gttaggccac cacttcaaga actctgtagc accgcctaca tacctcgctc tgctaatcct      6840
gttaccagtg gctgctgcca gtggcgataa gtcgtgtctt accgggttgg actcaagacg      6900
atagttaccg gataaggcgc agcggtcggg ctgaacgggg ggttcgtgca cacagcccag      6960
cttggagcga acgacctaca ccgaactgag atacctacag cgtgagctat gagaaagcgc      7020
cacgcttccc gaagggagaa aggcggacag gtatccggta agcggcaggg tcggaacagg      7080
agagcgcacg agggagcttc cagggggaaa cgcctggtat ctttatagtc ctgtcgggtt      7140
tcgccacctc tgacttgagc gtcgattttt gtgatgctcg tcaggggggc ggagcctatg      7200
gaaaaacgcc agcaacgcgg cctttttacg gttcctggcc ttttgctggc cttttgctca      7260
catgttcttt cctgcgttat cccctgattc tgtggataac cgtattaccg cctttgagtg      7320
agctgatacc gctcgccgca gccgaacgac cgagcgcagc gagtcagtga gcgaggaagc      7380
ggaagagcgc ccaatacgca aaccgcctct ccccgcgcgt tggccgattc attaatg         7437
```

(nucleotide sequence for BSP)

SEQ ID No. 2

```
atgcacgtgg cccagcctgc tgtggtactg gccagcagcc gaggcatcgc cagctttgtg        60
tgtgagtatg catctccagg caaatacact gaggtccggg tgacagtgct tcggcaggct       120
gacagccagg tgactgaagt ctgtgcggca acctacatga tggggaatga gttgaccttc       180
ctagatgatt ccatctgcac gggcacctcc agtggaaatc aagtgaacct cactatccaa       240
ggactgaggg ccatggacac gggactctac atctgcaagg tggagctcat gtacccaccg       300
ccatactacg agggcatagg caacggaacc cagatttatg taattgatcc agaaccgtgc       360
ccagattctg atcag                                                        375
```

(miRNA cassette)

SEQ ID NO. 3

```
ctggaggctt gctgaaggct gtatgctggc tcctccactt ggtggtttgg ttttggcctc        60
tgactgacca aaccacagtg gaggagccag gacacaaggc ctgttactag cactcacatg       120
gaacaaatgg cctctagcct ggaggcttgc tgaaggctgt atgctgtttc tcctggtatg       180
agatagcgtt ttggcctctg actgacgcta tctcaccagg agaaacagga cacaaggcct       240
gttactagca ctcacatgga acaaatggcc tctagcctgg aggcttgctg aaggctgtat       300
gctgccgcaa agtctaagta cttgggtttt ggcctctgac tgacccaagt acagactttg       360
cggcaggaca caaggcctgt tactagcact cacatggaac aaatggcctc tctagaa          417
```

(nucleotide sequence for 5' miRNA-155 #1-3'miRNA#1-155)

SEQ ID No. 4

```
ctggaggctt gctgaaggct gtatgctggc tcctccactt ggtggtttgg ttttggcctc        60
tgactgacca aaccacagtg gaggagccag gacacaaggc ctgttactag cactcacatg       120
```

-continued gaacaaatgg cc 132

(nucleotide sequence for 5' miRNA-155 #2-3'miRNA #2)

SEQ ID No. 5 ctggaggctt gctgaaggct gtatgctgtt tctcctggta tgagatagcg ttttggcctc 60
tgactgacgc tatctcacca ggagaaacag gacacaaggc ctgttactag cactcacatg 120
gaacaaatgg cc 132

(nucleotide sequence for 5' miRNA-155 #3-3' miRNA #3)

SEQ ID No. 6 ctggaggctt gctgaaggct gtatgctgcc gcaaagtcta agtacttggg ttttggcctc 60
tgactgaccc aagtacagac tttgcggcag gacacaaggc ctgttactag cactcacatg 120
gaacaaatgg cc 132

(miRNA 1 anti-sense)

SEQ ID No. 7 gctcctccac ttggtggttt g 21

(miRNA 1 sense)

SEQ ID No. 8 caaaccacag tggaggagc 19

(miRNA 2 anti-sense)

SEQ ID No. 9 tttctcctgg tatgagatag c 21

(miRNA 2 sense)

SEQ ID No. 10 gctatctcac caggagaaa 19

(miRNA 3 anti-sense)

SEQ ID No. 11 ccgcaaagtc taagtacttg g 21

(miRNA 3 sense)

SEQ ID No. 12 ccaagtacag actttgcgg 19

(nucleotide sequence for Start of whole RP to start of BSP)

SEQ ID No. 13 cagcagctgc gcgctcgctc gctcactgag gccgcccggg caaagcccgg gcgtcgggcg 60
acctttggtc gcccggcctc agtgagcgag cgagcgcgca gagagggagt ggccaactcc 120
atcactaggg gttccttgta gttaatgatt aacccgccat gctacttatc tacgtagcca 180
tgctctagga cattgattat tgactagtgg agttccgcgt tacataactt acggtaaatg 240
gcccgcctgg ctgaccgccc aacgaccccc gcccattgac gtcaataatg acgtatgttc 300
ccatagtaac gccaataggg actttccatt gacgtcaatg ggtggagtat ttacggtaaa 360
ctgcccactt ggcagtacat caagtgtatc atatgccaag tacgccccct attgacgtca 420
atgacggtaa atggcccgcc tggcattatg cccagtacat gaccttatgg gactttccta 480
cttggcagta catctacgta ttagtcatcg ctattaccat ggtcgaggtg agccccacgt 540
tctgcttcac tctccccatc tcccccccct ccccaccccc aattttgtat ttatttattt 600
tttaattatt ttgtgcagcg atgggggcgg gggggggggg gggcgcgcgc caggcggggc 660
ggggcggggc gaggggcggg gcggggcgag gcggagaggt gcggcggcag ccaatcagag 720
cggcgcgctc cgaaagtttc cttttatggc gaggcggcgg cggcggcggc cctataaaaa 780
gcgaagcgcg cggcgggcgg gagtcgctgc gcgctgcctt cgccccgtgc cccgctccgc 840
cgccgcctcg cgccgcccgc cccggctctg actgaccgcg ttactaaaac aggtaagtcc 900
ggcctccgcg ccgggttttg gcgcctcccg cgggcgcccc cctcctcacg gcgagcgctg 960
ccacgtcaga cgaagggcgc agcgagcgtc ctgatccttc cgcccggacg ctcaggacag 1020
cggcccgctg ctcataagac tcggccttag aaccccagta tcagcagaag gacattttag 1080

-continued

```
gacgggactt gggtgactct agggcactgg ttttctttcc agagagcgga acaggcgagg    1140
aaaagtagtc ccttctcggc gattctgcgg agggatctcc gtggggcggt gaacgccgat    1200
gatgcctcta ctaaccatgt tcatgttttc tttttttttc tacaggtcct gggtgacgaa    1260
cagggtaccg ccaccatggc caccggctct cgcacaagcc tgctgctggc tttcggactg    1320
ctgtgcctgc cttggctcca ggagggctcc gcc                                  1353
```

(nucleotide sequence for Start of whole RP to end of 3' miRNA #1)

SEQ ID No. 14

```
cagcagctgc gcgctcgctc gctcactgag gccgcccggg caaagcccgg gcgtcgggcg      60
acctttggtc gcccggcctc agtgagcgag cgagcgcgca gagagggagt ggccaactcc     120
atcactaggg gttccttgta gttaatgatt aacccgccat gctacttatc tacgtagcca     180
tgctctagga cattgattat tgactagtgg agttccgcgt tacataactt acggtaaatg     240
gcccgcctgg ctgaccgccc aacgaccccc gcccattgac gtcaataatg acgtatgttc     300
ccatagtaac gccaataggg actttccatt gacgtcaatg ggtggagtat ttacggtaaa     360
ctgcccactt ggcagtacat caagtgtatc atatgccaag tacgccccct attgacgtca     420
atgacggtaa atggcccgcc tggcattatg cccagtacat gaccttatgg gactttccta     480
cttggcagta catctacgta ttagtcatcg ctattaccat ggtcgaggtg agccccacgt     540
tctgcttcac tctccccatc tcccccccct ccccaccccc aattttgtat ttatttattt     600
tttaattatt ttgtgcagcg atgggggcgg gggggggggg gggcgcgcgc caggcggggc     660
ggggcggggc gaggggcggg gcggggcgag gcggagaggt gcggcggcag ccaatcagag     720
cggcgcgctc cgaaagtttc cttttatggc gaggcggcgg cggcggCggc cctataaaaa     780
gcgaagcgcg cggcgggcgg gagtcgctgc gcgctgcctt cgccccgtgc cccgctccgc     840
cgccgcctcg cgccgcccgc cccggctctg actgaccgcg ttactaaaac aggtaagtcc     900
ggcctccgcg ccgggttttg gcgcctcccg cgggcgcccc cctcctcacg gcgagcgctg     960
ccacgtcaga cgaagggcgc agcgagcgtc ctgatccttc cgcccggacg ctcaggacag    1020
cggcccgctg ctcataagac tcggccttag aaccccagta tcagcagaag gacattttag    1080
gacgggactt gggtgactct agggcactgg ttttctttcc agagagcgga acaggcgagg    1140
aaaagtagtc ccttctcggc gattctgcgg agggatctcc gtggggcggt gaacgccgat    1200
gatgcctcta ctaaccatgt tcatgttttc tttttttttc tacaggtcct gggtgacgaa    1260
cagggtaccg ccaccatggc caccggctct cgcacaagcc tgctgctggc tttcggactg    1320
ctgtgcctgc cttggctcca ggagggctcc gccatgcacg tggcccagcc tgctgtggta    1380
ctggccagca gccgaggcat cgccagcttt gtgtgtgagt atgcatctcc aggcaaatac    1440
actgaggtcc gggtgacagt gcttcggcag gctgacagcc aggtgactga agtctgtgcg    1500
gcaacctaca tgatggggaa tgagttgacc ttcctagatg attccatctg cacgggcacc    1560
tccagtggaa atcaagtgaa cctcactatc caaggactga gggccatgga cacgggactc    1620
tacatctgca aggtggagct catgtaccca ccgccatact acgagggcat aggcaacgga    1680
acccagattt atgtaattga tccagaaccg tgcccagatt ctgatcaggg atccggagga    1740
ggaggcagcg gaggaggcgg atctggcgga ggcggaagcg acaagaccca cacatgccca    1800
ccatgtcctg cacctgaact cctgggggga ccgtcagtct tcctcttccc cccaaaaccc    1860
aaggacaccc tcatgatctc ccggacccct gaggtcacat gcgtggtggt ggacgtgagc    1920
cacgaagacc ctgaggtcaa gttcaactgg tacgtggacg gcgtggaggt gcataatgcc    1980
aagacaaagc cgcgggagga gcagtacaac agcacgtacc gtgtggtcag cgtcctcacc    2040
gtcctgcacc aggactggct gaatggcaag gagtacaagt gcaaggtctc caacaaagcc    2100
```

-continued

```
ctcccagccc ccatcgagaa aaccatctcc aaagccaaag ggcagccccg agaaccacag     2160
gtgtacaccc tgcccccatc ccgggaggag atgaccaaga accaggtcag cctgacctgc     2220
ctggtcaaag gcttctatcc cagcgacatc gccgtggagt gggagagcaa tgggcagccg     2280
gagaacaact acaagaccac gcctcccgtg ctggactccg acggctcctt cttcctctac     2340
agcaagctca ccgtggacaa gagcaggtgg cagcagggga acgtcttctc atgctccgtg     2400
atgcatgagg ctctgcacaa ccactacacg cagaagagcc tctccctgtc tccgggtaaa     2460
taggctagca tcgataccgt cgctatgtgc tggaggcttg ctgaaggctg tatgctggct     2520
cctccacttg gtggtttggt tttggcctct gactgaccaa accacagtgg aggagccagg     2580
acacaaggcc tgttactagc actcacatgg aacaaatggc c                         2621
```

(nucleotide sequence for Start of whole RP to end of 3' miRNA #2)

SEQ ID No. 15

```
cagcagctgc gcgctcgctc gctcactgag gccgcccggg caaagcccgg gcgtcgggcg       60
acctttggtc gcccggcctc agtgagcgag cgagcgcgca gagagggagt ggccaactcc      120
atcactaggg gttccttgta gttaatgatt aacccgccat gctacttatc tacgtagcca      180
tgctctagga cattgattat tgactagtgg agttccgcgt tacataactt acggtaaatg      240
gcccgcctgg ctgaccgccc aacgaccccc gcccattgac gtcaataatg acgtatgttc      300
ccatagtaac gccaataggg actttccatt gacgtcaatg ggtggagtat ttacggtaaa      360
ctgcccactt ggcagtacat caagtgtatc atatgccaag tacgccccct attgacgtca      420
atgacggtaa atggcccgcc tggcattatg cccagtacat gaccttatgg gactttccta      480
cttggcagta catctacgta ttagtcatcg ctattaccat ggtcgaggtg agccccacgt      540
tctgcttcac tctccccatc tcccccccct ccccaccccc aattttgtat ttatttattt      600
tttaattatt ttgtgcagcg atgggggcgg gggggggggg gggcgcgcgc caggcggggc      660
ggggcggggc gaggggcggg gcggggcgag gcggagaggt gcggcggcag ccaatcagag      720
cggcgcgctc cgaaagtttc cttttatggc gaggcggcgg cggcggcggc cctataaaaa      780
gcgaagcgcg cggcgggcgg gagtcgctgc gcgctgcctt cgccccgtgc cccgctccgc      840
cgccgcctcg cgccgccgc cccggctctg actgaccgcg ttactaaaac aggtaagtcc      900
ggcctccgcg ccgggttttg gcgcctcccg cgggcgcccc cctcctcacg gcgagcgctg      960
ccacgtcaga cgaagggcgc agcgagcgtc ctgatccttc cgcccggacg ctcaggacag     1020
cggcccgctg ctcataagac tcggccttag aaccccagta tcagcagaag gacattttag     1080
gacgggactt gggtgactct agggcactgg ttttctttcc agagagcgga acaggcgagg     1140
aaaagtagtc ccttctcggc gattctgcgg agggatctcc gtggggcggt gaacgccgat     1200
gatgcctcta ctaaccatgt tcatgttttc tttttttttc tacaggtcct gggtgacgaa     1260
cagggtaccg ccaccatggc caccggctct cgcacaagcc tgctgctggc tttcggactg     1320
ctgtgcctgc cttggctcca ggagggctcc gccatgcacg tggcccagcc tgctgtggta     1380
ctggccagca gccgaggcat cgccagcttt gtgtgtgagt atgcatctcc aggcaaatac     1440
actgaggtcc gggtgacagt gcttcggcag gctgacagcc aggtgactga agtctgtgcg     1500
gcaacctaca tgatggggaa tgagttgacc ttcctagatg attccatctg cacgggcacc     1560
tccagtggaa atcaagtgaa cctcactatc caaggactga gggccatgga cacgggactc     1620
tacatctgca aggtggagct catgtaccca ccgccatact acgagggcat aggcaacgga     1680
acccagattt atgtaattga tccagaaccg tgcccagatt ctgatcaggg atccggagga     1740
ggaggcagcg gaggaggcgg atctggcgga ggcggaagcg acaagaccca cacatgccca     1800
```

-continued

```
ccatgtcctg cacctgaact cctgggggga ccgtcagtct tcctcttccc cccaaaaccc     1860
aaggacaccc tcatgatctc ccggacccct gaggtcacat gcgtggtggt ggacgtgagc     1920
cacgaagacc ctgaggtcaa gttcaactgg tacgtggacg gcgtggaggt gcataatgcc     1980
aagacaaagc cgcgggagga gcagtacaac agcacgtacc gtgtggtcag cgtcctcacc     2040
gtcctgcacc aggactggct gaatggcaag gagtacaagt gcaaggtctc caacaaagcc     2100
ctcccagccc ccatcgagaa aaccatctcc aaagccaaag ggcagccccg agaaccacag     2160
gtgtacaccc tgcccccatc ccgggaggag atgaccaaga accaggtcag cctgacctgc     2220
ctggtcaaag gcttctatcc cagcgacatc gccgtggagt gggagagcaa tgggcagccg     2280
gagaacaact acaagaccac gcctcccgtg ctggactccg acggctcctt cttcctctac     2340
agcaagctca ccgtggacaa gagcaggtgg cagcagggga acgtcttctc atgctccgtg     2400
atgcatgagg ctctgcacaa ccactacacg cagaagagcc tctccctgtc tccgggtaaa     2460
taggctagca tcgataccgt cgctatgtgc tggaggcttg ctgaaggctg tatgctggct     2520
cctccacttg gtggtttggt tttggcctct gactgaccaa accacagtgg aggagccagg     2580
acacaaggcc tgttactagc actcacatgg aacaaatggc ctctagcctg gaggcttgct     2640
gaaggctgta tgctgtttct cctggtatga gatagcgttt tggcctctga ctgacgctat     2700
ctcaccagga gaaacaggac acaaggcctg ttactagcac tcacatggaa caaatggcc      2759
```

(nucleotide sequence for Start of whole RP to end of 3' miRNA #3)

SEQ ID No. 16

```
cagcagctgc gcgctcgctc gctcactgag gccgcccggg caaagcccgg gcgtcgggcg       60
acctttggtc gcccggcctc agtgagcgag cgagcgcgca gagagggagt ggccaactcc      120
atcactaggg gttccttgta gttaatgatt aacccgccat gctacttatc tacgtagcca      180
tgctctagga cattgattat tgactagtgg agttccgcgt tacataactt acggtaaatg      240
gcccgcctgg ctgaccgccc aacgaccccc gcccattgac gtcaataatg acgtatgttc      300
ccatagtaac gccaataggg actttccatt gacgtcaatg ggtggagtat ttacggtaaa      360
ctgcccactt ggcagtacat caagtgtatc atatgccaag tacgccccct attgacgtca      420
atgacggtaa atggcccgcc tggcattatg cccagtacat gaccttatgg gactttccta      480
cttggcagta catctacgta ttagtcatcg ctattaccat ggtcgaggtg agccccacgt      540
tctgcttcac tctccccatc tcccccccct ccccaccccc aattttgtat ttatttattt      600
tttaattatt ttgtgcagcg atgggggcgg gggggggggg gggcgcgcgc caggcggggc      660
ggggcggggc gaggggcggg gcggggcgag gcggagaggt gcggcggcag ccaatcagag      720
cggcgcgctc cgaaagtttc cttttatggc gaggcggcgg cggcggcggc cctataaaaa      780
gcgaagcgcg cggcgggcgg gagtcgctgc gcgctgcctt cgccccgtgc cccgctccgc      840
cgccgcctcg cgccgccgc cccggctctg actgaccgcg ttactaaaac aggtaagtcc      900
ggcctccgcg ccgggttttg gcgcctcccg cgggcgcccc cctcctcacg gcgagcgctg      960
ccacgtcaga cgaagggcgc agcgagcgtc ctgatccttc cgcccggacg ctcaggacag     1020
cggcccgctg ctcataagac tcggccttag aaccccagta tcagcagaag gacattttag     1080
gacgggactt gggtgactct agggcactgg ttttctttcc agagagcgga acaggcgagg     1140
aaaagtagtc ccttctcggc gattctgcgg agggatctcc gtggggcggt gaacgccgat     1200
gatgcctcta ctaaccatgt tcatgttttc tttttttttc tacaggtcct gggtgacgaa     1260
cagggtaccg ccaccatggc caccggctct cgcacaagcc tgctgctggc tttcggactg     1320
ctgtgcctgc cttggctcca ggagggctcc gccatgcacg tggcccagcc tgctgtggta     1380
ctggccagca gccgaggcat cgccagcttt gtgtgtgagt atgcatctcc aggcaaatac     1440
```

-continued actgaggtcc gggtgacagt gcttcggcag gctgacagcc aggtgactga agtctgtgcg 1500
gcaacctaca tgatggggaa tgagttgacc ttcctagatg attccatctg cacgggcacc 1560
tccagtggaa atcaagtgaa cctcactatc caaggactga gggccatgga cacgggactc 1620
tacatctgca aggtggagct catgtaccca ccgccatact acgagggcat aggcaacgga 1680
acccagattt atgtaattga tccagaaccg tgcccagatt ctgatcaggg atccggagga 1740
ggaggcagcg gaggaggcgg atctggcgga ggcggaagcg acaagaccca cacatgccca 1800
ccatgtcctg cacctgaact cctgggggga ccgtcagtct tcctcttccc cccaaaaccc 1860
aaggacaccc tcatgatctc ccggacccct gaggtcacat gcgtggtggt ggacgtgagc 1920
cacgaagacc ctgaggtcaa gttcaactgg tacgtggacg gcgtggaggt gcataatgcc 1980
aagacaaagc cgcgggagga gcagtacaac agcacgtacc gtgtggtcag cgtcctcacc 2040
gtcctgcacc aggactggct gaatggcaag gagtacaagt gcaaggtctc caacaaagcc 2100
ctcccagccc ccatcgagaa aaccatctcc aaagccaaag ggcagccccg agaaccacag 2160
gtgtacaccc tgcccccatc ccgggaggag atgaccaaga accaggtcag cctgacctgc 2220
ctggtcaaag gcttctatcc cagcgacatc gccgtggagt gggagagcaa tgggcagccg 2280
gagaacaact acaagaccac gcctcccgtg ctggactccg acggctcctt cttcctctac 2340
agcaagctca ccgtggacaa gagcaggtgg cagcagggga acgtcttctc atgctccgtg 2400
atgcatgagg ctctgcacaa ccactacacg cagaagagcc tctccctgtc tccgggtaaa 2460
taggctagca tcgataccgt cgctatgtgc tggaggcttg ctgaaggctg tatgctggct 2520
cctccacttg gtggtttggt tttggcctct gactgaccaa accacagtgg aggagccagg 2580
acacaaggcc tgttactagc actcacatgg aacaaatggc ctctagcctg gaggcttgct 2640
gaaggctgta tgctgtttct cctggtatga gatagcgttt tggcctctga ctgacgctat 2700
ctcaccagga gaaacaggac acaaggcctg ttactagcac tcacatggaa caaatggcct 2760
ctagcctgga ggcttgctga aggctgtatg ctgccgcaaa gtctaagtac ttgggttttg 2820
gcctctgact gacccaagta cagactttgc ggcaggacac aaggcctgtt actagcactc 2880
acatggaaca aatggcc 2897

(inverted terminal repeat #1)

SEQ ID No. 17 ctgcgcgctc gctcgctcac tgaggccgcc cgggcaaagc ccgggcgtcg ggcgaccttt 60
ggtcgcccgg cctcagtgag cgagcgagcg cgcagagagg gagtggccaa ctccatcact 120
aggggttcct 130

(ITR #1 to ITR #2)

SEQ ID No. 18 cagcagctgc gcgctcgctc gctcactgag gccgcccggg caaagcccgg gcgtcgggcg 60
acctttggtc gcccggcctc agtgagcgag cgagcgcgca gagagggagt ggccaactcc 120
atcactaggg gttccttgta gttaatgatt aacccgccat gctacttatc tacgtagcca 180
tgctctagga cattgattat tgactagtgg agttccgcgt tacataactt acggtaaatg 240
gcccgcctgg ctgaccgccc aacgaccccc gcccattgac gtcaataatg acgtatgttc 300
ccatagtaac gccaataggg actttccatt gacgtcaatg ggtggagtat ttacggtaaa 360
ctgcccactt ggcagtacat caagtgtatc atatgccaag tacgccccct attgacgtca 420
atgacggtaa atggcccgcc tggcattatg cccagtacat gaccttatgg gactttccta 480
cttggcagta catctacgta ttagtcatcg ctattaccat ggtcgaggtg agccccacgt 540
tctgcttcac tctccccatc tcccccccct ccccaccccc aattttgtat ttatttattt 600

-continued

```
tttaattatt ttgtgcagcg atgggggcgg gggggggggg gggcgcgcgc caggcggggc     660
ggggcggggc gaggggcggg gcggggcgag gcggagaggt gcggcggcag ccaatcagag     720
cggcgcgctc cgaaagtttc cttttatggc gaggcggcgg cggcggcggc cctataaaaa     780
gcgaagcgcg cggcgggcgg gagtcgctgc gcgctgcctt cgccccgtgc cccgctccgc     840
cgccgcctcg cgccgcccgc cccggctctg actgaccgcg ttactaaaac aggtaagtcc     900
ggcctccgcg ccgggttttg gcgcctcccg cgggcgcccc cctcctcacg gcgagcgctg     960
ccacgtcaga cgaagggcgc agcgagcgtc ctgatccttc cgcccggacg ctcaggacag    1020
cggcccgctg ctcataagac tcggccttag aaccccagta tcagcagaag gacattttag    1080
gacgggactt gggtgactct agggcactgg ttttctttcc agagagcgga acaggcgagg    1140
aaaagtagtc ccttctcggc gattctgcgg agggatctcc gtggggcggt gaacgccgat    1200
gatgcctcta ctaaccatgt tcatgttttc tttttttttc tacaggtcct gggtgacgaa    1260
cagggtaccg ccaccatggc caccggctct cgcacaagcc tgctgctggc tttcggactg    1320
ctgtgcctgc cttggctcca ggagggctcc gccatgcacg tggcccagcc tgctgtggta    1380
ctggccagca gccgaggcat cgccagcttt gtgtgtgagt atgcatctcc aggcaaatac    1440
actgaggtcc gggtgacagt gcttcggcag gctgacagcc aggtgactga agtctgtgcg    1500
gcaacctaca tgatggggaa tgagttgacc ttcctagatg attccatctg cacgggcacc    1560
tccagtggaa atcaagtgaa cctcactatc caaggactga gggccatgga cacgggactc    1620
tacatctgca aggtggagct catgtaccca ccgccatact acgagggcat aggcaacgga    1680
acccagattt atgtaattga tccagaaccg tgcccagatt ctgatcaggg atccggagga    1740
ggaggcagcg gaggaggcgg atctggcgga ggcggaagcg acaagaccca cacatgccca    1800
ccatgtcctg cacctgaact cctgggggga ccgtcagtct tcctcttccc cccaaaaccc    1860
aaggacaccc tcatgatctc ccggacccct gaggtcacat gcgtggtggt ggacgtgagc    1920
cacgaagacc ctgaggtcaa gttcaactgg tacgtggacg gcgtggaggt gcataatgcc    1980
aagacaaagc cgcgggagga gcagtacaac agcacgtacc gtgtggtcag cgtcctcacc    2040
gtcctgcacc aggactggct gaatggcaag gagtacaagt gcaaggtctc caacaaagcc    2100
ctcccagccc ccatcgagaa aaccatctcc aaagccaaag ggcagccccg agaaccacag    2160
gtgtacaccc tgcccccatc ccgggaggag atgaccaaga accaggtcag cctgacctgc    2220
ctggtcaaag gcttctatcc cagcgacatc gccgtggagt gggagagcaa tgggcagccg    2280
gagaacaact acaagaccac gcctcccgtg ctggactccg acggctcctt cttcctctac    2340
agcaagctca ccgtggacaa gagcaggtgg cagcagggga acgtcttctc atgctccgtg    2400
atgcatgagg ctctgcacaa ccactacacg cagaagagcc tctccctgtc tccgggtaaa    2460
taggctagca tcgataccgt cgctatgtgc tggaggcttg ctgaaggctg tatgctggct    2520
cctccacttg gtggtttggt tttggcctct gactgaccaa accacagtgg aggagccagg    2580
acacaaggcc tgttactagc actcacatgg aacaaatggc ctctagcctg gaggcttgct    2640
gaaggctgta tgctgtttct cctggtatga gatagcgttt tggcctctga ctgacgctat    2700
ctcaccagga gaaacaggac acaaggcctg ttactagcac tcacatggaa caaatggcct    2760
ctagcctgga ggcttgctga aggctgtatg ctgccgcaaa gtctaagtac ttgggttttg    2820
gcctctgact gacccaagta cagactttgc ggcaggacac aaggcctgtt actagcactc    2880
acatggaaca aatggcctct ctagaataat caacctctgg attacaaaat ttgtgaaaga    2940
ttgactggta ttcttaacta tgttgctcct tttacgctat gtggatacgc tgctttaatg    3000
cctttgtatc atgctattgc ttcccgtatg gctttcattt tctcctcctt gtataaatcc    3060
```

-continued

```
tggttgctgt ctctttatga ggagttgtgg cccgttgtca ggcaacgtgg cgtggtgtgc     3120

actgtgtttg ctgacgcaac ccccactggt tggggcattg ccaccacctg tcagctcctt     3180

tccgggactt tcgctttccc cctccctatt gccacggcgg aactcatcgc cgcctgcctt     3240

gcccgctgct ggacaggggc tcggctgttg ggcactgaca attccgtggt gttgtcgggg     3300

aaatcatcgt cctttccttg gctgctcgcc tgtgttgcca cctggattct gcgcgggacg     3360

tccttctgct acgtcccttc ggccctcaat ccagcggacc ttccttcccg cggcctgctg     3420

ccggctctgc ggcctcttcc gcgtcttcgc cttcgccctc agacgagtcg gatctccctt     3480

tgggccgcct ccccgcctaa gcttatcgat accgtcgaga tctaacttgt ttattgcagc     3540

ttataatggt tacaaataaa gcaatagcat cacaaatttc acaaataaag catttttttc     3600

actgcattct agttgtggtt tgtccaaact catcaatgta tcttatcatg tctggatctc     3660

gacctcgact agagcatggc tacgtagata agtagcatgg cgggttaatc attaactaca     3720

aggaacccct agtgatggag ttggccactc cctctctgcg cgctcgctcg ctcactgagg     3780

ccgggcgacc aaaggtcgcc cgacgcccgg gctttgcccg ggcggcctca gtgagcgagc     3840

gagcgcgcag                                                             3850
```

(inverted terminal repeat #2)

SEQ ID No. 19

```
aggaacccct agtgatggag ttggccactc cctctctgcg cgctcgctcg ctcactgagg       60

ccgggcgacc aaaggtcgcc cgacgcccgg gctttgcccg ggcggcctca gtgagcgagc      120

gagcgcgcag                                                             130
```

(amino acid sequence for BSP produced per SEQ ID No. 2)

SEQ ID No. 20

```
Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Tyr Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Glu Gly Ile Gly Asn Gly Thr Gln Ile
            100                 105                 110

Tyr Val Ile Asp Pro Glu Pro Cys Pro Asp Ser Asp Gln
        115                 120                 125
```

Example 1—Expression Cassette

Expression cassettes for expressing a monoclonal antibody (mAb) and/or a protein and/or miRNA were synthesized by Genscript. Each cassette contained a signal peptide, the variable heavy domain, the human IgG1 constant domain, the protein or the miRNA sequence followed by (when it is an Ab), a self-cleaving 2A peptide sequence, a signal peptide, the variable light domain and the human lambda constant domain. The synthesized mAb and/or protein and/or miRNA expression cassettes were cloned into the pAVA-00200 plasmid backbone containing the CASI promoter1, multiple cloning site (MCS), Woodchuck Hepatitis Virus post-transcriptional regulatory element (WPRE), Simian virus 40 (SV40) polyadenylation (polyA) sequence all flanked by the AAV2 inverted terminal repeats (ITR). pAVA-00200 was cut with the restriction enzymes KpnI and XbaI in the MCS and separated on a 1% agarose gel. The band of interest was excised and purified using a gel extraction kit. Each mAb and/or protein and/or miRNA expression cassette was amplified by PCR using Taq polymerase and the PCR products were gel purified and the bands on interest were also excised and purified using a gel extraction kit. These PCR products contained the mAb and/or protein and/or miRNA expression cassettes in addition to 15 base pair 5' and 3' overhangs that align with the ends of the linearized pAVA-00200 backbone. Using in-fusion cloning2, the amplified mAb or protein or miRNA expression cassettes are integrated with the pAVA-00200 backbone via homologous recombination. The resulting plasmid vectors contained the following 5' ITR, CASI promoter, monoclonal antibody or protein or miRNA expression cassette, WPRE, SV40 polyA and ITR 3', per SEQ ID No. 1 and as shown in FIG. 1 and as shown in fourteen contiguous portions in FIG. 2 through FIG. 15.

Example 2—Animal Studies

C57BL/6 mice and BALB/c mice were purchased from Charles River. AAV vectors of Example 1 were administered to 6-week-old C57BL/6 mice with the exception of the AAV vector that encoded mAb expression, which was tested in BALB/c mice. All animal experiments were approved by the institutional animal care committees of the Canadian Science Centre for Human and Animal Health and the University of Guelph. Intramuscular or intraorgan administration of the AAV were performed using a 29-gauge needle and a 40-μL injection volume. Injection into the tail vein was performed on mice that were warmed slightly, using a 100-μL injection volume. Intranasal administration of the AAV vectors were performed using a 40-μL injection volume. The dose used was about $2\times10^{11}$ vector genomes per mouse.

Example 3—Experimental Data

Figure 17:
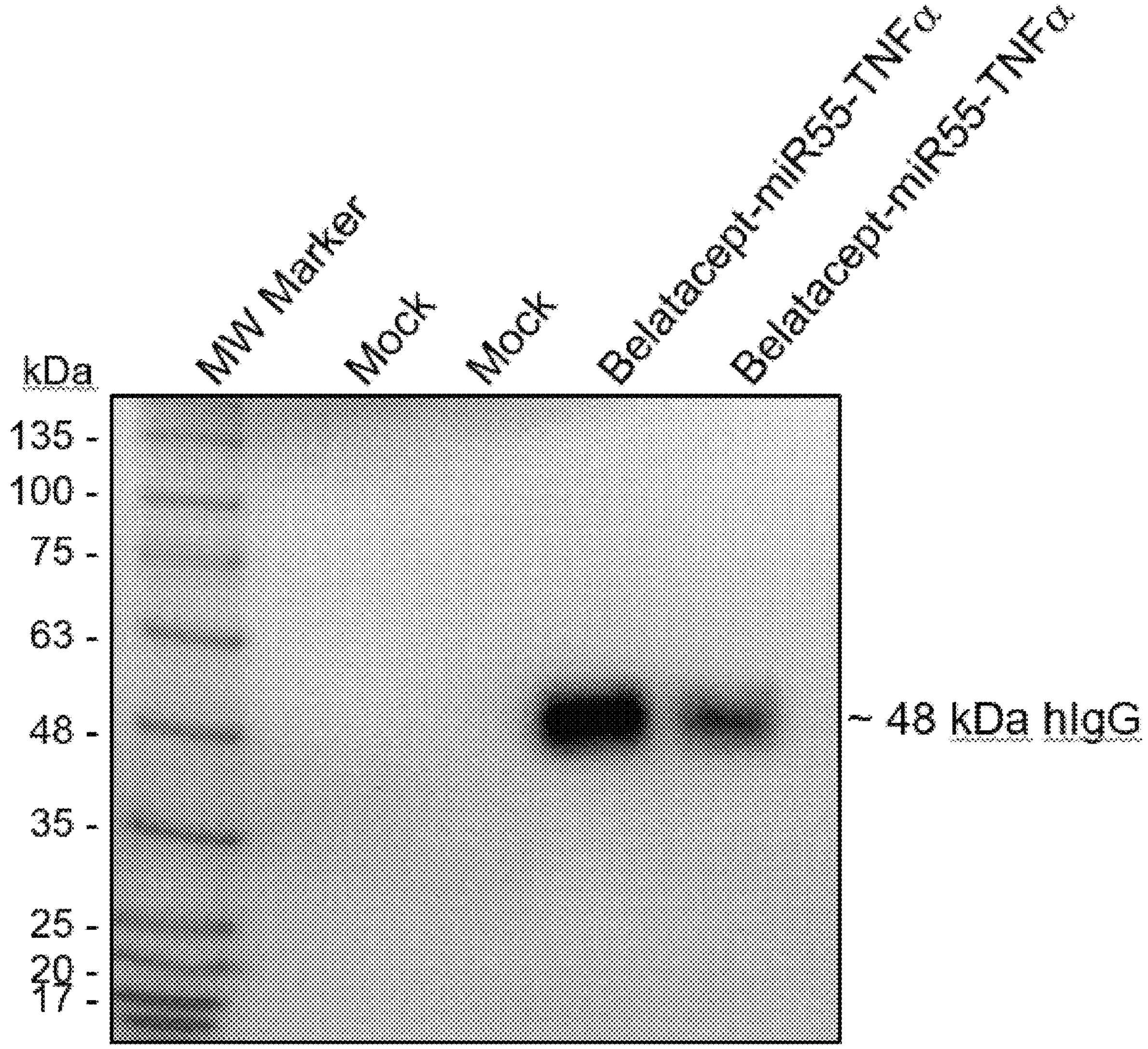
FIG. 17 is an image of belatacept-similar protein analysis obtained from muscle samples of mice treated with an embodiment of the present disclosure.

FIG. 17 is an image of a Western blot gel that shows BSP expression in samples taken from muscle of mice administered i.m. (gastrocnemius muscle) $1\times10^{11}$ vg of the composition of SEQ ID No. 1. The samples were taken 28 days post-administration. Lysates were probed with an anti-hIgG1 antibody. Lane 1 is a molecular weight marker, lane 2 is a mock sample, lane 3 is a further mock sample, lanes 4 and 5 are samples taken from mice administered the composition with SEQ ID No. 1. The BSP proteins can be seen in as a gel migrant with an approximate molecular weight of 48 kDa in lanes 4 and 5, whereas samples obtains from mock administered mice (lanes 2 and 3) did not show any gel migratory bands at 48 kDa. Without being bound by any particular theory, administering the composition induced mice to produce BSP.

Figure 18:
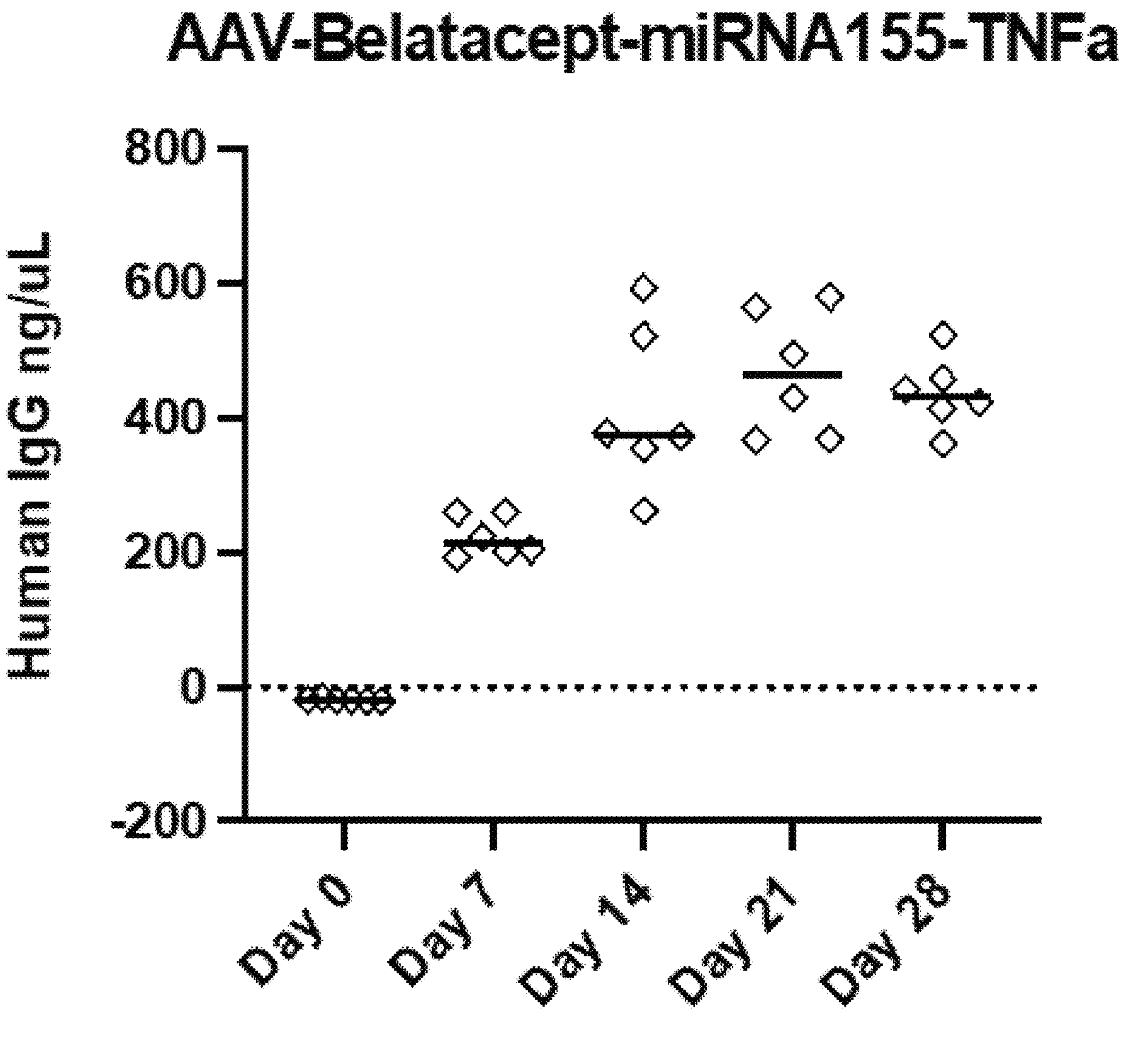
FIG. 18 is a scatter plot of human IgG data over time taken from muscle samples of mice treated with an embodiment of the present disclosure.

FIG. 18 shows a scatter plot of human IgG (ng/4) measured in plasma samples obtained at day 0, 7, 14, 21 and 28 post-administration of the composition with of SEQ ID No. 1. The plasma samples were analyzed using a commercially available human IgG quantitative ELISA (Abcam cat no. 195215). Without being bound by any particular theory, administering the composition induced mice to produce human IgG 1.

Example 4—In Vitro Studies

Figure 19:
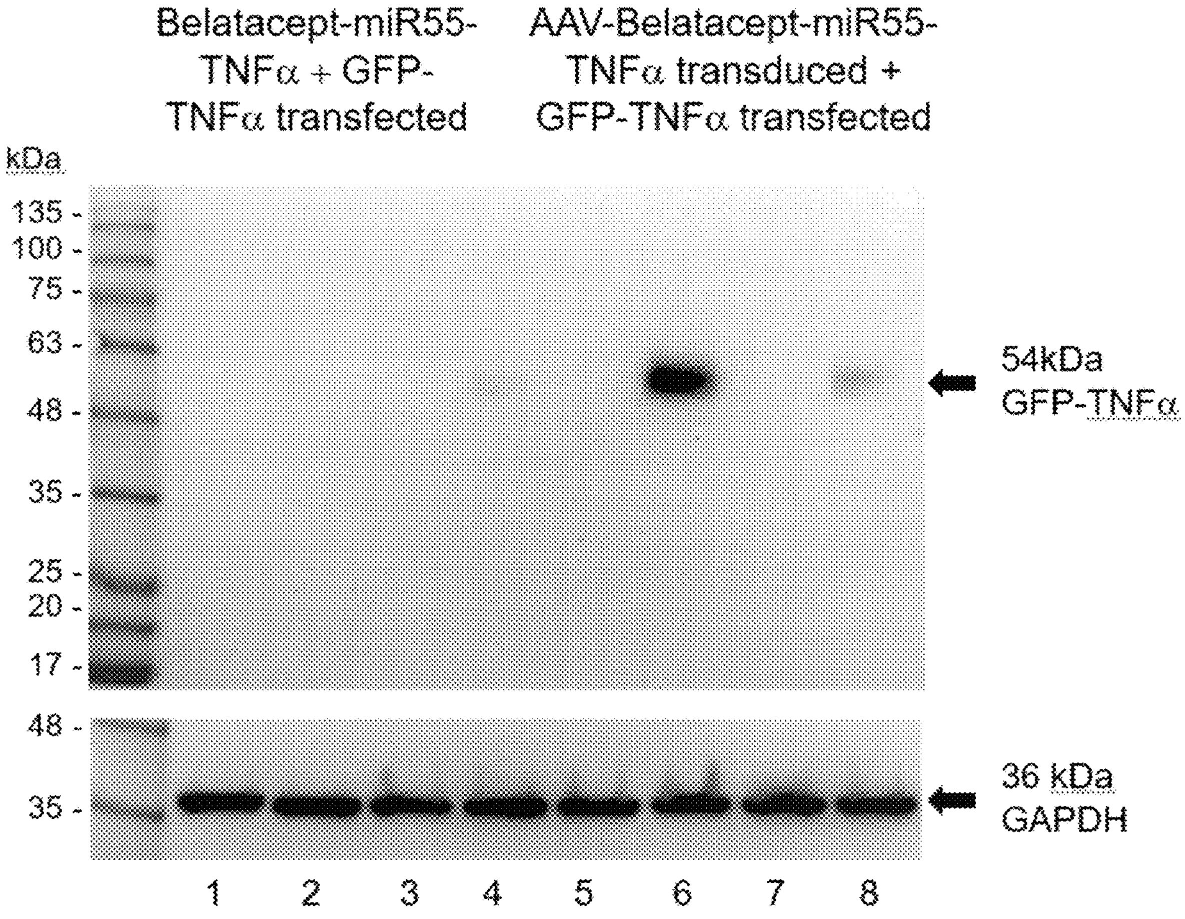
FIG. 19 is an image of tumor necrosis factor alpha protein analysis obtained from muscle samples of mice treated with an embodiment of the present disclosure.

FIG. 19 is an image of another Western blot gel that shows a reduction in recombinant TNF-α expression in HEK293 cells transduced with the RP of SEQ ID NO. 1, 5 days prior to transfection with a mammalian expression vector encoding murine TNF-α fused to a green fluorescence protein (GFP) and harvested 3 days later. In order to obtain samples for protein analysis, lysates were probed with an anti-murine TNF-α antibody. In the image of the gel, lanes 1 and 5 each contained mock samples, lanes 2 and 6 each contained a sample taken from GFP-TNF-α transfected cells, lanes 3 and 7 contain samples from cells transfected with the composition of SEQ ID No. 1 and lanes 4 and 8 contain samples from cells transfected with the vector of SEQ ID No. 1 and the GFP-TNF-α. The bottom portion of the gel image shows gel migratory bands that correspond with an anti-GAPDH antibody, demonstrating substantially equal loading of total protein in the gel lanes. The samples with GFP-TNF-α show a gel migrant with an approximate molecular weight of 54 kDa. Without being bound by any particular theory, these results demonstrate efficacy of miRNA-based gene-silencing of TNF-α production. The engineered miRNAs produced by the miR155 fully complement their target site and cleave the target mRNA, in this case TNF-α leading to a reduction in TNF-α protein expression.

Table 1 below shows the expression levels of TNF-alpha (ag) measured in HEK293 cells transduced with an AAV that included a nucleotide sequence that encoded for TNF-alpha siRNA, TNF-alpha miRNA or the BSP and TNF-alpha miRNA (SEQ ID No. 1) or a respective control.

TABLE 1

TNF-Alpha expression following administration of three AAVs.

| | Control (ag) | AAV recipient (ag) | P-value |
|---|---|---|---|
| TNF-alpha siRNA | 12 | 2 | 0.0151 |
| TNF-alpha miRNA | 2273 | 130 | <0.001 |
| TNF-alpha miRNA/BSP | 2311 | 142 | <0.001 |

SEQUENCE LISTING

```
Sequence total quantity: 20
SEQ ID NO: 1            moltype = DNA  length = 7437
FEATURE                 Location/Qualifiers
misc_feature            1..7437
                        note = Synthetic Sequence
source                  1..7437
                        mol_type = other DNA
                        organism = synthetic construct
SEQUENCE: 1
cagcagctgc gcgctcgctc gctcactgag gccgcccggg caaagcccgg gcgtcgggcg  60
acctttggtc gcccggcctc agtgagcgag cgagcgcgca gagagggagt ggccaactcc  120
atcactaggg gttccttgta gttaatgatt aacccgccat gctacttatc tacgtagcca  180
tgctctagga cattgattat tgactagtgg agttccgcgt tacataactt acggtaaatg  240
gcccgcctgg ctgaccgccc aacgaccccc gcccattgac gtcaataatg acgtatgttc  300
ccatagtaac gccaataggg actttccatt gacgtcaatg ggtggagtat ttacggtaaa  360
ctgcccactt ggcagtacat caagtgtatc atatgccaag tacgccccct attgacgtca  420
atgacggtaa atggcccgcc tggcattatg cccagtacat gaccttatgg gactttccta  480
cttggcagta catctacgta ttagtcatcg ctattaccat ggtcgaggtg agccccacgt  540
tctgcttcac tctccccatc tcccccccct ccccaccccc aattttgtat ttatttattt  600
```

-continued

```
tttaattatt ttgtgcagcg atgggggcgg gggggggggg gggcgcgcgc caggcggggc  660
ggggcggggc gaggggcggg gcggggcgag gcggagaggt gcggcggcag ccaatcagag  720
cggcgcgctc cgaaagtttc cttttatggc gaggcggcgg cggcggcggc cctataaaaa  780
gcgaagcgcg cggcgggcgg gagtcgctgc gcgctgcctt cgccccgtgc cccgctccgc  840
cgccgcctcg cgccgcccgc cccggctctg actgaccgcg ttactaaaac aggtaagtcc  900
ggcctccgcg ccgggttttg gcgcctcccg cgggcgcccc cctcctcacg gcgagcgctg  960
ccacgtcaga cgaagggcgc agcgagcgtc ctgatccttc cgcccggacg ctcaggacag  1020
cggcccgctg ctcataagac tcggccttag aaccccagta tcagcagaag gacattttag  1080
gacgggactt gggtgactct agggcactgg ttttctttcc agagagcgga acaggcgagg  1140
aaaagtagtc ccttctcggc gattctgcgg agggatctcc gtggggcggt gaacgccgat  1200
gatgcctcta ctaaccatgt tcatgttttc tttttttttc tacaggtcct gggtgacgaa  1260
cagggtaccg ccaccatggc caccggctct cgcacaagcc tgctgctggc tttcggactg  1320
ctgtgcctgc cttggctcca ggagggctcc gccatgcacg tggcccagcc tgctgtggta  1380
ctggccagca gccgaggcat cgccagcttt gtgtgtgagt atgcatctcc aggcaaatac  1440
actgaggtcc gggtgacagt gcttcggcag gctgacagcc aggtgactga agtctgtgcg  1500
gcaacctaca tgatggggaa tgagttgacc ttcctagatg attccatctg cacgggcacc  1560
tccagtggaa atcaagtgaa cctcactatc caaggactga gggccatgga cacgggactc  1620
tacatctgca aggtggagct catgtaccca ccgccatact acgagggcat aggcaacgga  1680
acccagattt atgtaattga tccagaaccg tgcccagatt ctgatcaggg atccggagga  1740
ggaggcagcg gaggaggcgg atctggcgga ggcggaagcg acaagaccca cacatgccca  1800
ccatgtcctg cacctgaact cctgggggga ccgtcagtct tcctcttccc cccaaaaccc  1860
aaggacaccc tcatgatctc ccggacccct gaggtcacat gcgtggtggt ggacgtgagc  1920
cacgaagacc ctgaggtcaa gttcaactgg tacgtggacg gcgtggaggt gcataatgcc  1980
aagacaaagc cgcgggagga gcagtacaac agcacgtacc gtgtggtcag cgtcctcacc  2040
gtcctgcacc aggactggct gaatggcaag gagtacaagt gcaaggtctc caacaaagcc  2100
ctcccagccc ccatcgagaa aaccatctcc aaagccaaag ggcagccccg agaaccacag  2160
gtgtacaccc tgcccccatc ccgggaggag atgaccaaga accaggtcag cctgacctgc  2220
ctggtcaaag gcttctatcc cagcgacatc gccgtggagt gggagagcaa tgggcagccg  2280
gagaacaact acaagaccac gcctcccgtg ctggactccg acggctcctt cttcctctac  2340
agcaagctca ccgtggacaa gagcaggtgg cagcagggga acgtcttctc atgctccgtg  2400
atgcatgagg ctctgcacaa ccactacacg cagaagagcc tctccctgtc tccgggtaaa  2460
taggctagca tcgataccgt cgctatgtgc tggaggcttg ctgaaggctg tatgctggct  2520
cctccacttg gtggtttggt tttggcctct gactgaccaa accacagtgg aggagccagg  2580
acacaaggcc tgttactagc actcacatgg aacaaatggc ctctagcctg gaggcttgct  2640
gaaggctgta tgctgtttct cctggtatga gatagcgttt tggcctctga ctgacgctat  2700
ctcaccagga gaaacaggac acaaggcctg ttactagcac tcacatggaa caaatggcct  2760
ctagcctgga ggcttgctga aggctgtatg ctgccgcaaa gtctaagtac ttgggttttg  2820
gcctctgact gacccaagta cagactttgc ggcaggacac aaggcctgtt actagcactc  2880
acatggaaca aatggcctct ctagaataat caacctctgg attacaaaat ttgtgaaaga  2940
ttgactggta ttcttaacta tgttgctcct tttacgctat gtggatacgc tgctttaatg  3000
cctttgtatc atgctattgc ttcccgtatg gctttcattt tctcctcctt gtataaatcc  3060
tggttgctgt ctctttatga ggagttgtgg cccgttgtca ggcaacgtgg cgtggtgtgc  3120
actgtgtttg ctgacgcaac ccccactggt tggggcattg ccaccacctg tcagctcctt  3180
tccgggactt tcgctttccc cctccctatt gccacggcgg aactcatcgc cgcctgcctt  3240
gcccgctgct ggacaggggc tcggctgttg ggcactgaca attccgtggt gttgtcgggg  3300
aaatcatcgt cctttccttg gctgctcgcc tgtgttgcca cctggattct gcgcgggacg  3360
tccttctgct acgtcccttc ggccctcaat ccagcggacc ttccttcccg cggcctgctg  3420
ccggctctgc ggcctcttcc gcgtcttcgc cttcgccctc agacgagtcg gatctccctt  3480
tgggccgcct ccccgcctaa gcttatcgat accgtcgaga tctaacttgt ttattgcagc  3540
ttataatggt tacaaataaa gcaatagcat cacaaatttc acaaataaag catttttttc  3600
actgcattct agttgtggtt tgtccaaact catcaatgta tcttatcatg tctggatctc  3660
gacctcgact agagcatggc tacgtagata agtagcatgg cgggttaatc attaactaca  3720
aggaacccct agtgatggag ttggccactc cctctctgcg cgctcgctcg ctcactgagg  3780
ccgggcgacc aaaggtcgcc cgacgcccgg gctttgcccg ggcggcctca gtgagcgagc  3840
gagcgcgcag ctggcgtaat agcgaagagg cccgcaccga tcgcccttcc caacagttgc  3900
gcagcctgaa tggcgaatgg cgattccgtt gcaatggctg gcggtaatat tgttctggat  3960
attaccagca aggccgatag tttgagttct tctactcagg caagtgatgt tattactaat  4020
caaagaagta ttgcgacaac ggttaatttg cgtgatggac agactctttt actcggtggc  4080
ctcactgatt ataaaaacac ttctcaggat tctggcgtac cgttcctgtc taaaatccct  4140
ttaatcggcc tcctgtttag ctcccgctct gattctaacg aggaaagcac gttatacgtg  4200
ctcgtcaaag caaccatagt acgcgccctg tagcggcgca ttaagcgcgg cgggtgtggt  4260
ggttacgcgc agcgtgaccg ctacacttgc cagcgcccta gcgcccgctc ctttcgcttt  4320
cttcccttcc tttctcgcca cgttcgccgg ctttccccgt caagctctaa atcgggggct  4380
ccctttaggg ttccgattta gtgctttacg gcacctcgac cccaaaaaac ttgattaggg  4440
tgatggttca cgtagtgggc catcgccctg atagacggtt tttcgccctt tgacgttgga  4500
gtccacgttc tttaatagtg gactcttgtt ccaaactgga acaacactca accctatctc  4560
ggtctattct tttgatttat aagggatttt gccgatttcg gcctattggt taaaaaatga  4620
gctgatttaa caaaaattta acgcgaattt taacaaaata ttaacgttta caatttaaat  4680
atttgcttat acaatcttcc tgtttttggg gcttttctga ttatcaaccg gggtacatat  4740
gattgacatg ctagttttac gattaccgtt catcgattct cttgtttgct ccagactctc  4800
aggcaatgac ctgatagcct ttgtagagac ctctcaaaaa tagctaccct ctccggcatg  4860
aatttatcag ctagaacggt tgaatatcat attgatggtg atttgactgt ctccggcctt  4920
tctcacccgt ttgaatcttt acctacacat tactcaggca ttgcatttaa aatatatgag  4980
ggttctaaaa atttttatcc ttgcgttgaa ataaaggctt ctcccgcaaa agtattacag  5040
ggtcataatg tttttggtac aaccgattta gctttatgct ctgaggcttt attgcttaat  5100
tttgctaatt ctttgccttg cctgtatgat ttattggatg ttggaattcc tgatgcggta  5160
ttttctcctt acgcatctgt gcggtatttc acaccgcata tggtgcactc tcagtacaat  5220
ctgctctgat gccgcatagt taagccagcc ccgacacccg ccaacacccg ctgacgcgcc  5280
ctgacgggct tgtctgctcc cggcatccgc ttacagacaa gctgtgaccg tctccgggag  5340
```

-continued

```
ctgcatgtgt cagaggtttt caccgtcatc accgaaacgc gcgagacgaa agggcctcgt  5400
gatacgccta tttttatagg ttaatgtcat gataataatg gtttcttaga cgtcaggtgg  5460
cacttttcgg ggaaatgtgc gcggaacccc tatttgttta tttttctaaa tacattcaaa  5520
tatgtatccg ctcatgagac aataaccctg ataaatgctt caataatatt gaaaaaggaa  5580
gagtatgagt attcaacatt tccgtgtcgc ccttattccc ttttttgcgg cattttgcct  5640
tcctgttttt gctcacccag aaacgctggt gaaagtaaaa gatgctgaag atcagttggg  5700
tgcacgagtg ggttacatcg aactggatct caacagcggt aagatccttg agagttttcg  5760
ccccgaagaa cgttttccaa tgatgagcac ttttaaagtt ctgctatgtg gcgcggtatt  5820
atcccgtatt gacgccgggc aagagcaact cggtcgccgc atacactatt ctcagaatga  5880
cttggttgag tactcaccag tcacagaaaa gcatcttacg gatggcatga cagtaagaga  5940
attatgcagt gctgccataa ccatgagtga taacactgcg gccaacttac ttctgacaac  6000
gatcggagga ccgaaggagc taaccgcttt tttgcacaac atgggggatc atgtaactcg  6060
ccttgatcgt tgggaaccgg agctgaatga agccatacca aacgacgagc gtgacaccac  6120
gatgcctgta gcaatggcaa caacgttgcg caaactatta actggcgaac tacttactct  6180
agcttcccgg caacaattaa tagactggat ggaggcggat aaagttgcag gaccacttct  6240
gcgctcggcc cttccggctg gctggtttat tgctgataaa tctggagccg gtgagcgtgg  6300
gtctcgcggt atcattgcag cactggggcc agatggtaag ccctcccgta tcgtagttat  6360
ctacacgacg gggagtcagg caactatgga tgaacgaaat agacagatcg ctgagatagg  6420
tgcctcactg attaagcatt ggtaactgtc agaccaagtt tactcatata tactttagat  6480
tgatttaaaa cttcattttt aatttaaaag gatctaggtg aagatccttt ttgataatct  6540
catgaccaaa atcccttaac gtgagttttc gttccactga gcgtcagacc ccgtagaaaa  6600
gatcaaagga tcttcttgag atcctttttt tctgcgcgta atctgctgct tgcaaacaaa  6660
aaaaccaccg ctaccagcgg tggtttgttt gccggatcaa gagctaccaa ctctttttcc  6720
gaaggtaact ggcttcagca gagcgcagat accaaatact gtccttctag tgtagccgta  6780
gttaggccac cacttcaaga actctgtagc accgcctaca tacctcgctc tgctaatcct  6840
gttaccagtg gctgctgcca gtggcgataa gtcgtgtctt accgggttgg actcaagacg  6900
atagttaccg gataaggcgc agcggtcggg ctgaacgggg ggttcgtgca cacagcccag  6960
cttggagcga acgacctaca ccgaactgag atacctacag cgtgagctat gagaaagcgc  7020
cacgcttccc gaagggagaa aggcggacag gtatccggta agcggcaggg tcggaacagg  7080
agagcgcacg agggagcttc caggggggaaa cgcctggtat ctttatagtc ctgtcgggtt  7140
tcgccacctc tgacttgagc gtcgattttt gtgatgctcg tcaggggggc ggagcctatg  7200
gaaaaacgcc agcaacgcgg cctttttacg gttcctggcc ttttgctggc cttttgctca  7260
catgttcttt cctgcgttat cccctgattc tgtggataac cgtattaccg cctttgagtg  7320
agctgatacc gctcgccgca gccgaacgac cgagcgcagc gagtcagtga gcgaggaagc  7380
ggaagagcgc ccaatacgca aaccgcctct ccccgcgcgt tggccgattc attaatg     7437

SEQ ID NO: 2            moltype = DNA  length = 375
FEATURE                 Location/Qualifiers
misc_feature            1..375
                        note = Synthetic Sequence
source                  1..375
                        mol_type = other DNA
                        organism = synthetic construct
SEQUENCE: 2
atgcacgtgg cccagcctgc tgtggtactg gccagcagcc gaggcatcgc cagctttgtg  60
tgtgagtatg catctccagg caaatacact gaggtccggg tgacagtgct tcggcaggct  120
gacagccagg tgactgaagt ctgtgcggca acctacatga tggggaatga gttgaccttc  180
ctagatgatt ccatctgcac gggcacctcc agtggaaatc aagtgaacct cactatccaa  240
ggactgaggg ccatggacac gggactctac atctgcaagg tggagctcat gtacccaccg  300
ccatactacg agggcatagg caacggaacc cagatttatg taattgatcc agaaccgtgc  360
ccagattctg atcag                                                   375

SEQ ID NO: 3            moltype = DNA  length = 417
FEATURE                 Location/Qualifiers
misc_feature            1..417
                        note = Synthetic Sequence
source                  1..417
                        mol_type = other DNA
                        organism = synthetic construct
SEQUENCE: 3
ctggaggctt gctgaaggct gtatgctggc tcctccactt ggtggtttgg ttttggcctc  60
tgactgacca aaccacagtg gaggagccag gacacaaggc ctgttactag cactcacatg  120
gaacaaatgg cctctagcct ggaggcttgc tgaaggctgt atgctgtttc tcctggtatg  180
agatagcgtt ttggcctctg actgacgcta tctcaccagg agaaacagga cacaaggcct  240
gttactagca ctcacatgga acaaatggcc tctagcctgg aggcttgctg aaggctgtat  300
gctgccgcaa agtctaagta cttgggtttt ggcctctgac tgacccaagt acagactttg  360
cggcaggaca caaggcctgt tactagcact cacatggaac aaatggcctc tctagaa     417

SEQ ID NO: 4            moltype = DNA  length = 132
FEATURE                 Location/Qualifiers
misc_feature            1..132
                        note = Synthetic Sequence
source                  1..132
                        mol_type = other DNA
                        organism = synthetic construct
SEQUENCE: 4
ctggaggctt gctgaaggct gtatgctggc tcctccactt ggtggtttgg ttttggcctc  60
tgactgacca aaccacagtg gaggagccag gacacaaggc ctgttactag cactcacatg  120
gaacaaatgg cc                                                      132
```

-continued

```
SEQ ID NO: 5            moltype = DNA  length = 132
FEATURE                 Location/Qualifiers
misc_feature            1..132
                        note = Synthetic Sequence
source                  1..132
                        mol_type = other DNA
                        organism = synthetic construct
SEQUENCE: 5
ctggaggctt gctgaaggct gtatgctgtt tctcctggta tgagatagcg ttttggcctc  60
tgactgacgc tatctcacca ggagaaacag gacacaaggc ctgttactag cactcacatg  120
gaacaaatgg cc                                                      132

SEQ ID NO: 6            moltype = DNA  length = 132
FEATURE                 Location/Qualifiers
misc_feature            1..132
                        note = Synthetic Sequence
source                  1..132
                        mol_type = other DNA
                        organism = synthetic construct
SEQUENCE: 6
ctggaggctt gctgaaggct gtatgctgcc gcaaagtcta agtacttggg ttttggcctc  60
tgactgaccc aagtacagac tttgcggcag gacacaaggc ctgttactag cactcacatg  120
gaacaaatgg cc                                                      132

SEQ ID NO: 7            moltype = DNA  length = 21
FEATURE                 Location/Qualifiers
misc_feature            1..21
                        note = Synthetic Sequence
source                  1..21
                        mol_type = other DNA
                        organism = synthetic construct
SEQUENCE: 7
gctcctccac ttggtggttt g                                            21

SEQ ID NO: 8            moltype = DNA  length = 19
FEATURE                 Location/Qualifiers
misc_feature            1..19
                        note = Synthetic Sequence
source                  1..19
                        mol_type = other DNA
                        organism = synthetic construct
SEQUENCE: 8
caaaccacag tggaggagc                                               19

SEQ ID NO: 9            moltype = DNA  length = 21
FEATURE                 Location/Qualifiers
misc_feature            1..21
                        note = Synthetic Sequence
source                  1..21
                        mol_type = other DNA
                        organism = synthetic construct
SEQUENCE: 9
tttctcctgg tatgagatag c                                            21

SEQ ID NO: 10           moltype = DNA  length = 19
FEATURE                 Location/Qualifiers
misc_feature            1..19
                        note = Synthetic Sequence
source                  1..19
                        mol_type = other DNA
                        organism = synthetic construct
SEQUENCE: 10
gctatctcac caggagaaa                                               19

SEQ ID NO: 11           moltype = DNA  length = 21
FEATURE                 Location/Qualifiers
misc_feature            1..21
                        note = Synthetic Sequence
source                  1..21
                        mol_type = other DNA
                        organism = synthetic construct
SEQUENCE: 11
ccgcaaagtc taagtacttg g                                            21

SEQ ID NO: 12           moltype = DNA  length = 19
FEATURE                 Location/Qualifiers
misc_feature            1..19
                        note = Synthetic Sequence
```

-continued

```
source                  1..19
                        mol_type = other DNA
                        organism = synthetic construct
SEQUENCE: 12
ccaagtacag actttgcgg                                              19

SEQ ID NO: 13           moltype = DNA  length = 1353
FEATURE                 Location/Qualifiers
misc_feature            1..1353
                        note = Synthetic Sequence
source                  1..1353
                        mol_type = other DNA
                        organism = synthetic construct
SEQUENCE: 13
cagcagctgc gcgctcgctc gctcactgag gccgcccggg caaagcccgg gcgtcgggcg  60
acctttggtc gcccggcctc agtgagcgag cgagcgcgca gagagggagt ggccaactcc  120
atcactaggg gttccttgta gttaatgatt aacccgccat gctacttatc tacgtagcca  180
tgctctagga cattgattat tgactagtgg agttccgcgt tacataactt acggtaaatg  240
gcccgcctgg ctgaccgccc aacgaccccc gcccattgac gtcaataatg acgtatgttc  300
ccatagtaac gccaataggg actttccatt gacgtcaatg ggtggagtat ttacggtaaa  360
ctgcccactt ggcagtacat caagtgtatc atatgccaag tacgccccct attgacgtca  420
atgacggtaa atggcccgcc tggcattatg cccagtacat gaccttatgg gactttccta  480
cttggcagta catctacgta ttagtcatcg ctattaccat ggtcgaggtg agccccacgt  540
tctgcttcac tctccccatc tcccccccct ccccaccccc aattttgtat ttatttattt  600
tttaattatt ttgtgcagcg atgggggcgg gggggggggg gggcgcgcgc caggcggggc  660
ggggcggggc gaggggcggg gcggggcgag gcggagaggt gcggcggcag ccaatcagag  720
cggcgcgctc cgaaagtttc cttttatggc gaggcggcgg cggcggcggc cctataaaaa  780
gcgaagcgcg cggcgggcgg gagtcgctgc gcgctgcctt cgccccgtgc cccgctccgc  840
cgccgcctcg cgccgcccgc cccggctctg actgaccgcg ttactaaaac aggtaagtcc  900
ggcctccgcg ccgggttttg gcgcctcccg cgggcgcccc cctcctcacg gcgagcgctg  960
ccacgtcaga cgaagggcgc agcgagcgtc ctgatccttc cgcccggacg ctcaggacag  1020
cggcccgctg ctcataagac tcggccttag aaccccagta tcagcagaag gacattttag  1080
gacgggactt gggtgactct agggcactgg ttttctttcc agagagcgga acaggcgagg  1140
aaaagtagtc ccttctcggc gattctgcgg agggatctcc gtggggcggt gaacgccgat  1200
gatgcctcta ctaaccatgt tcatgttttc ttttttttc tacaggtcct gggtgacgaa  1260
cagggtaccg ccaccatggc caccggctct cgcacaagcc tgctgctggc tttcggactg  1320
ctgtgcctgc cttggctcca ggagggctcc gcc                              1353

SEQ ID NO: 14           moltype = DNA  length = 2621
FEATURE                 Location/Qualifiers
misc_feature            1..2621
                        note = Synthetic Sequence
source                  1..2621
                        mol_type = other DNA
                        organism = synthetic construct
SEQUENCE: 14
cagcagctgc gcgctcgctc gctcactgag gccgcccggg caaagcccgg gcgtcgggcg  60
acctttggtc gcccggcctc agtgagcgag cgagcgcgca gagagggagt ggccaactcc  120
atcactaggg gttccttgta gttaatgatt aacccgccat gctacttatc tacgtagcca  180
tgctctagga cattgattat tgactagtgg agttccgcgt tacataactt acggtaaatg  240
gcccgcctgg ctgaccgccc aacgaccccc gcccattgac gtcaataatg acgtatgttc  300
ccatagtaac gccaataggg actttccatt gacgtcaatg ggtggagtat ttacggtaaa  360
ctgcccactt ggcagtacat caagtgtatc atatgccaag tacgccccct attgacgtca  420
atgacggtaa atggcccgcc tggcattatg cccagtacat gaccttatgg gactttccta  480
cttggcagta catctacgta ttagtcatcg ctattaccat ggtcgaggtg agccccacgt  540
tctgcttcac tctccccatc tcccccccct ccccaccccc aattttgtat ttatttattt  600
tttaattatt ttgtgcagcg atgggggcgg gggggggggg gggcgcgcgc caggcggggc  660
ggggcggggc gaggggcggg gcggggcgag gcggagaggt gcggcggcag ccaatcagag  720
cggcgcgctc cgaaagtttc cttttatggc gaggcggcgg cggcggcggc cctataaaaa  780
gcgaagcgcg cggcgggcgg gagtcgctgc gcgctgcctt cgccccgtgc cccgctccgc  840
cgccgcctcg cgccgcccgc cccggctctg actgaccgcg ttactaaaac aggtaagtcc  900
ggcctccgcg ccgggttttg gcgcctcccg cgggcgcccc cctcctcacg gcgagcgctg  960
ccacgtcaga cgaagggcgc agcgagcgtc ctgatccttc cgcccggacg ctcaggacag  1020
cggcccgctg ctcataagac tcggccttag aaccccagta tcagcagaag gacattttag  1080
gacgggactt gggtgactct agggcactgg ttttctttcc agagagcgga acaggcgagg  1140
aaaagtagtc ccttctcggc gattctgcgg agggatctcc gtggggcggt gaacgccgat  1200
gatgcctcta ctaaccatgt tcatgttttc ttttttttc tacaggtcct gggtgacgaa  1260
cagggtaccg ccaccatggc caccggctct cgcacaagcc tgctgctggc tttcggactg  1320
ctgtgcctgc cttggctcca ggagggctcc gccatgcacg tggcccagcc tgctgtggta  1380
ctggccagca gccgaggcat cgccagcttt gtgtgtgagt atgcatctcc aggcaaatac  1440
actgaggtcc gggtgacagt gcttcggcag gctgacagcc aggtgactga agtctgtgcg  1500
gcaacctaca tgatggggaa tgagttgacc ttcctagatg attccatctg cacgggcacc  1560
tccagtggaa atcaagtgaa cctcactatc caaggactga gggccatgga cacgggactc  1620
tacatctgca aggtggagct catgtaccca ccgccatact acgagggcat aggcaacgga  1680
acccagattt atgtaattga tccagaaccg tgcccagatt ctgatcaggg atccggagga  1740
ggaggcagcg gaggaggcgg atctggcgga ggcggaagcg acaagaccca cacatgccca  1800
ccatgtcctg cacctgaact cctgggggga ccgtcagtct tcctcttccc cccaaaaccc  1860
aaggacaccc tcatgatctc ccggacccct gaggtcacat gcgtggtggt ggacgtgagc  1920
cacgaagacc ctgaggtcaa gttcaactgg tacgtggacg gcgtggaggt gcataatgcc  1980
```

```
aagacaaagc cgcgggagga gcagtacaac agcacgtacc gtgtggtcag cgtcctcacc  2040
gtcctgcacc aggactggct gaatggcaag gagtacaagt gcaaggtctc caacaaagcc  2100
ctcccagccc ccatcgagaa aaccatctcc aaagccaaag ggcagccccg agaaccacag  2160
gtgtacaccc tgcccccatc ccgggaggag atgaccaaga accaggtcag cctgacctgc  2220
ctggtcaaag gcttctatcc cagcgacatc gccgtggagt gggagagcaa tgggcagccg  2280
gagaacaact acaagaccac gcctcccgtg ctggactccg acggctcctt cttcctctac  2340
agcaagctca ccgtggacaa gagcaggtgg cagcagggga acgtcttctc atgctccgtg  2400
atgcatgagg ctctgcacaa ccactacacg cagaagagcc tctccctgtc tccgggtaaa  2460
taggctagca tcgataccgt cgctatgtgc tggaggcttg ctgaaggctg tatgctggct  2520
cctccacttg gtggtttggt tttggcctct gactgaccaa accacagtgg aggagccagg  2580
acacaaggcc tgttactagc actcacatgg aacaaatggc c                      2621

SEQ ID NO: 15          moltype = DNA  length = 2759
FEATURE                Location/Qualifiers
misc_feature           1..2759
                       note = Synthetic Sequence
source                 1..2759
                       mol_type = other DNA
                       organism = synthetic construct
SEQUENCE: 15
cagcagctgc gcgctcgctc gctcactgag gccgcccggg caaagcccgg gcgtcgggcg  60
acctttggtc gcccggcctc agtgagcgag cgagcgcgca gagagggagt ggccaactcc  120
atcactaggg gttccttgta gttaatgatt aacccgccat gctacttatc tacgtagcca  180
tgctctagga cattgattat tgactagtgg agttccgcgt tacataactt acggtaaatg  240
gcccgcctgg ctgaccgccc aacgaccccc gcccattgac gtcaataatg acgtatgttc  300
ccatagtaac gccaataggg actttccatt gacgtcaatg ggtggagtat ttacggtaaa  360
ctgcccactt ggcagtacat caagtgtatc atatgccaag tacgccccct attgacgtca  420
atgacggtaa atggcccgcc tggcattatg cccagtacat gaccttatgg gactttccta  480
cttggcagta catctacgta ttagtcatcg ctattaccat ggtcgaggtg agccccacgt  540
tctgcttcac tctccccatc tcccccccct ccccaccccc aattttgtat ttatttattt  600
tttaattatt ttgtgcagcg atgggggcgg gggggggggg gggcgcgcgc caggcggggc  660
ggggcggggc gaggggcggg gcggggcgag gcggagaggt gcggcggcag ccaatcagag  720
cggcgcgctc cgaaagtttc cttttatggc gaggcggcgg cggcggcggc cctataaaaa  780
gcgaagcgcg cggcgggcgg gagtcgctgc gcgctgcctt cgccccgtgc cccgctccgc  840
cgccgcctcg cgccgcccgc cccggctctg actgaccgcg ttactaaaac aggtaagtcc  900
ggcctccgcg ccgggttttg gcgcctcccg cgggcgcccc cctcctcacg gcgagcgctg  960
ccacgtcaga cgaagggcgc agcgagcgtc ctgatccttc cgcccggacg ctcaggacag  1020
cggcccgctg ctcataagac tcggccttag aaccccagta tcagcagaag gacattttag  1080
gacgggactt gggtgactct agggcactgg ttttctttcc agagagcgga acaggcgagg  1140
aaaagtagtc ccttctcggc gattctgcgg agggatctcc gtggggcggt gaacgccgat  1200
gatgcctcta ctaaccatgt tcatgttttc tttttttttc tacaggtcct gggtgacgaa  1260
cagggtaccg ccaccatggc caccggctct cgcacaagcc tgctgctggc tttcggactg  1320
ctgtgcctgc cttggctcca ggagggctcc gccatgcacg tggcccagcc tgctgtggta  1380
ctggccagca gccgaggcat cgccagcttt gtgtgtgagt atgcatctcc aggcaaatac  1440
actgaggtcc gggtgacagt gcttcggcag gctgacagcc aggtgactga agtctgtgcg  1500
gcaacctaca tgatggggaa tgagttgacc ttcctagatg attccatctg cacgggcacc  1560
tccagtggaa atcaagtgaa cctcactatc caaggactga gggccatgga cacgggactc  1620
tacatctgca aggtggagct catgtaccca ccgccatact acgagggcat aggcaacgga  1680
acccagattt atgtaattga tccagaaccg tgcccagatt ctgatcaggg atccggagga  1740
ggaggcagcg gaggaggcgg atctggcgga ggcggaagcg acaagaccca cacatgccca  1800
ccatgtcctg cacctgaact cctgggggga ccgtcagtct tcctcttccc cccaaaaccc  1860
aaggacaccc tcatgatctc ccggacccct gaggtcacat gcgtggtggt ggacgtgagc  1920
cacgaagacc ctgaggtcaa gttcaactgg tacgtggacg gcgtggaggt gcataatgcc  1980
aagacaaagc cgcgggagga gcagtacaac agcacgtacc gtgtggtcag cgtcctcacc  2040
gtcctgcacc aggactggct gaatggcaag gagtacaagt gcaaggtctc caacaaagcc  2100
ctcccagccc ccatcgagaa aaccatctcc aaagccaaag ggcagccccg agaaccacag  2160
gtgtacaccc tgcccccatc ccgggaggag atgaccaaga accaggtcag cctgacctgc  2220
ctggtcaaag gcttctatcc cagcgacatc gccgtggagt gggagagcaa tgggcagccg  2280
gagaacaact acaagaccac gcctcccgtg ctggactccg acggctcctt cttcctctac  2340
agcaagctca ccgtggacaa gagcaggtgg cagcagggga acgtcttctc atgctccgtg  2400
atgcatgagg ctctgcacaa ccactacacg cagaagagcc tctccctgtc tccgggtaaa  2460
taggctagca tcgataccgt cgctatgtgc tggaggcttg ctgaaggctg tatgctggct  2520
cctccacttg gtggtttggt tttggcctct gactgaccaa accacagtgg aggagccagg  2580
acacaaggcc tgttactagc actcacatgg aacaaatggc ctctagcctg gaggcttgct  2640
gaaggctgta tgctgtttct cctggtatga gatagcgttt tggcctctga ctgacgctat  2700
ctcaccagga gaaacaggac acaaggcctg ttactagcac tcacatggaa caaatggcc   2759

SEQ ID NO: 16          moltype = DNA  length = 2897
FEATURE                Location/Qualifiers
misc_feature           1..2897
                       note = Synthetic Sequence
source                 1..2897
                       mol_type = other DNA
                       organism = synthetic construct
SEQUENCE: 16
cagcagctgc gcgctcgctc gctcactgag gccgcccggg caaagcccgg gcgtcgggcg  60
acctttggtc gcccggcctc agtgagcgag cgagcgcgca gagagggagt ggccaactcc  120
atcactaggg gttccttgta gttaatgatt aacccgccat gctacttatc tacgtagcca  180
tgctctagga cattgattat tgactagtgg agttccgcgt tacataactt acggtaaatg  240
```

-continued

```
gcccgcctgg ctgaccgccc aacgaccccc gcccattgac gtcaataatg acgtatgttc  300
ccatagtaac gccaataggg actttccatt gacgtcaatg ggtggagtat ttacggtaaa  360
ctgcccactt ggcagtacat caagtgtatc atatgccaag tacgccccct attgacgtca  420
atgacggtaa atggcccgcc tggcattatg cccagtacat gaccttatgg gactttccta  480
cttggcagta catctacgta ttagtcatcg ctattaccat ggtcgaggtg agccccacgt  540
tctgcttcac tctccccatc tcccccccct ccccaccccc aattttgtat ttatttattt  600
tttaattatt ttgtgcagcg atgggggcgg gggggggggg ggggcgcgcgc caggcggggc  660
ggggcggggc gaggggcggg gcggggcgag gcggagaggt gcggcggcag ccaatcagag  720
cggcgcgctc cgaaagtttc cttttatggc gaggcggcgg cggcggcggc cctataaaaa  780
gcgaagcgcg cggcgggcgg gagtcgctgc gcgctgcctt cgccccgtgc cccgctccgc  840
cgccgcctcg cgccgcccgc cccggctctg actgaccgcg ttactaaaac aggtaagtcc  900
ggcctccgcg ccgggttttg gcgcctcccg cgggcgcccc cctcctcacg gcgagcgctg  960
ccacgtcaga cgaagggcgc agcgagcgtc ctgatccttc cgcccggacg ctcaggacag  1020
cggcccgctg ctcataagac tcggccttag aaccccagta tcagcagaag gacattttag  1080
gacgggactt gggtgactct agggcactgg ttttctttcc agagagcgga acaggcgagg  1140
aaaagtagtc ccttctcggc gattctgcgg agggatctcc gtggggcggt gaacgccgat  1200
gatgcctcta ctaaccatgt tcatgttttc tttttttttc tacaggtcct gggtgacgaa  1260
cagggtaccg ccaccatggc caccggctct cgcacaagcc tgctgctggc tttcggactg  1320
ctgtgcctgc cttggctcca ggagggctcc gccatgcacg tggcccagcc tgctgtggta  1380
ctggccagca gccgaggcat cgccagcttt gtgtgtgagt atgcatctcc aggcaaatac  1440
actgaggtcc gggtgacagt gcttcggcag gctgacagcc aggtgactga agtctgtgcg  1500
gcaacctaca tgatggggaa tgagttgacc ttcctagatg attccatctg cacgggcacc  1560
tccagtggaa atcaagtgaa cctcactatc caaggactga gggccatgga cacgggactc  1620
tacatctgca aggtggagct catgtaccca ccgccatact acgagggcat aggcaacgga  1680
acccagattt atgtaattga tccagaaccg tgcccagatt ctgatcaggg atccggagga  1740
ggaggcagcg gaggaggcgg atctggcgga ggcggaagcg acaagaccca cacatgccca  1800
ccatgtcctg cacctgaact cctgggggga ccgtcagtct tcctcttccc cccaaaaccc  1860
aaggacaccc tcatgatctc ccggacccct gaggtcacat gcgtggtggt ggacgtgagc  1920
cacgaagacc ctgaggtcaa gttcaactgg tacgtggacg gcgtggaggt gcataatgcc  1980
aagacaaagc cgcgggagga gcagtacaac agcacgtacc gtgtggtcag cgtcctcacc  2040
gtcctgcacc aggactggct gaatggcaag gagtacaagt gcaaggtctc caacaaagcc  2100
ctcccagccc ccatcgagaa aaccatctcc aaagccaaag ggcagccccg agaaccacag  2160
gtgtacaccc tgcccccatc ccgggaggag atgaccaaga accaggtcag cctgacctgc  2220
ctggtcaaag gcttctatcc cagcgacatc gccgtggagt gggagagcaa tgggcagccg  2280
gagaacaact acaagaccac gcctcccgtg ctggactccg acggctcctt cttcctctac  2340
agcaagctca ccgtggacaa gagcaggtgg cagcagggga acgtcttctc atgctccgtg  2400
atgcatgagg ctctgcacaa ccactacacg cagaagagcc tctccctgtc tccgggtaaa  2460
taggctagca tcgataccgt cgctatgtgc tggaggcttg ctgaaggctg tatgctggct  2520
cctccacttg gtggtttggt tttggcctct gactgaccaa accacagtgg aggagccagg  2580
acacaaggcc tgttactagc actcacatgg aacaaatggc ctctagcctg gaggcttgct  2640
gaaggctgta tgctgtttct cctggtatga gatagcgttt tggcctctga ctgacgctat  2700
ctcaccagga gaaacaggac acaaggcctg ttactagcac tcacatggaa caaatggcct  2760
ctagcctgga ggcttgctga aggctgtatg ctgccgcaaa gtctaagtac ttgggttttg  2820
gcctctgact gacccaagta cagactttgc ggcaggacac aaggcctgtt actagcactc  2880
acatggaaca aatggcc                                                 2897

SEQ ID NO: 17          moltype = DNA  length = 130
FEATURE                Location/Qualifiers
misc_feature           1..130
                       note = Synthetic Sequence
source                 1..130
                       mol_type = other DNA
                       organism = synthetic construct
SEQUENCE: 17
ctgcgcgctc gctcgctcac tgaggccgcc cgggcaaagc ccgggcgtcg ggcgaccttt  60
ggtcgcccgg cctcagtgag cgagcgagcg cgcagagagg gagtggccaa ctccatcact  120
aggggttcct                                                        130

SEQ ID NO: 18          moltype = DNA  length = 130
FEATURE                Location/Qualifiers
misc_feature           1..130
                       note = Synthetic Sequence
source                 1..130
                       mol_type = other DNA
                       organism = synthetic construct
SEQUENCE: 18
aggaacccct agtgatggag ttggccactc cctctctgcg cgctcgctcg ctcactgagg  60
ccgggcgacc aaaggtcgcc cgacgcccgg gctttgcccg ggcggcctca gtgagcgagc  120
gagcgcgcag                                                        130

SEQ ID NO: 19          moltype = DNA  length = 3850
FEATURE                Location/Qualifiers
misc_feature           1..3850
                       note = Synthetic Sequence
source                 1..3850
                       mol_type = other DNA
                       organism = synthetic construct
SEQUENCE: 19
cagcagctgc gcgctcgctc gctcactgag gccgcccggg caaagcccgg gcgtcgggcg  60
```

-continued

```
acctttggtc gcccggcctc agtgagcgag cgagcgcgca gagagggagt ggccaactcc  120
atcactaggg gttccttgta gttaatgatt aacccgccat gctacttatc tacgtagcca  180
tgctctagga cattgattat tgactagtgg agttccgcgt tacataactt acggtaaatg  240
gcccgcctgg ctgaccgccc aacgaccccc gcccattgac gtcaataatg acgtatgttc  300
ccatagtaac gccaataggg actttccatt gacgtcaatg ggtggagtat ttacggtaaa  360
ctgcccactt ggcagtacat caagtgtatc atatgccaag tacgccccct attgacgtca  420
atgacggtaa atggcccgcc tggcattatg cccagtacat gaccttatgg gactttccta  480
cttggcagta catctacgta ttagtcatcg ctattaccat ggtcgaggtg agccccacgt  540
tctgcttcac tctccccatc tcccccccct ccccaccccc aattttgtat ttatttattt  600
tttaattatt ttgtgcagcg atgggggcgg gggggggggg gggcgcgcgc caggcggggc  660
ggggcggggc gaggggcggg gcggggcgag gcggagaggt gcggcggcag ccaatcagag  720
cggcgcgctc cgaaagtttc cttttatggc gaggcggcgg cggcggcggc cctataaaaa  780
gcgaagcgcg cggcgggcgg gagtcgctgc gcgctgcctt cgccccgtgc cccgctccgc  840
cgccgcctcg cgccgcccgc cccggctctg actgaccgcg ttactaaaac aggtaagtcc  900
ggcctccgcg ccgggttttg gcgcctcccg cgggcgcccc cctcctcacg gcgagcgctg  960
ccacgtcaga cgaagggcgc agcgagcgtc ctgatccttc cgcccggacg ctcaggacag  1020
cggcccgctg ctcataagac tcggccttag aaccccagta tcagcagaag gacattttag  1080
gacgggactt gggtgactct agggcactgg ttttctttcc agagagcgga acaggcgagg  1140
aaaagtagtc ccttctcggc gattctgcgg agggatctcc gtggggcggt gaacgccgat  1200
gatgcctcta ctaaccatgt tcatgttttc tttttttttc tacaggtcct gggtgacgaa  1260
cagggtaccg ccaccatggc caccggctct cgcacaagcc tgctgctggc tttcggactg  1320
ctgtgcctgc cttggctcca ggagggctcc gccatgcacg tggcccagcc tgctgtggta  1380
ctggccagca gccgaggcat cgccagcttt gtgtgtgagt atgcatctcc aggcaaatac  1440
actgaggtcc gggtgacagt gcttcggcag gctgacagcc aggtgactga agtctgtgcg  1500
gcaacctaca tgatggggaa tgagttgacc ttcctagatg attccatctg cacgggcacc  1560
tccagtggaa atcaagtgaa cctcactatc caaggactga gggccatgga cacgggactc  1620
tacatctgca aggtggagct catgtaccca ccgccatact acgagggcat aggcaacgga  1680
acccagattt atgtaattga tccagaaccg tgcccagatt ctgatcaggg atccggagga  1740
ggaggcagcg gaggaggcgg atctggcgga ggcggaagcg acaagaccca cacatgccca  1800
ccatgtcctg cacctgaact cctgggggga ccgtcagtct tcctcttccc cccaaaaccc  1860
aaggacaccc tcatgatctc ccggacccct gaggtcacat gcgtggtggt ggacgtgagc  1920
cacgaagacc ctgaggtcaa gttcaactgg tacgtggacg gcgtggaggt gcataatgcc  1980
aagacaaagc cgcgggagga gcagtacaac agcacgtacc gtgtggtcag cgtcctcacc  2040
gtcctgcacc aggactggct gaatggcaag gagtacaagt gcaaggtctc caacaaagcc  2100
ctcccagccc ccatcgagaa aaccatctcc aaagccaaag ggcagccccg agaaccacag  2160
gtgtacaccc tgcccccatc ccgggaggag atgaccaaga accaggtcag cctgacctgc  2220
ctggtcaaag gcttctatcc cagcgacatc gccgtggagt gggagagcaa tgggcagccg  2280
gagaacaact acaagaccac gcctcccgtg ctggactccg acggctcctt cttcctctac  2340
agcaagctca ccgtggacaa gagcaggtgg cagcagggga acgtcttctc atgctccgtg  2400
atgcatgagg ctctgcacaa ccactacacg cagaagagcc tctccctgtc tccgggtaaa  2460
taggctagca tcgataccgt cgctatgtgc tggaggcttg ctgaaggctg tatgctggct  2520
cctccacttg gtggtttggt tttggcctct gactgaccaa accacagtgg aggagccagg  2580
acacaaggcc tgttactagc actcacatgg aacaaatggc ctctagcctg gaggcttgct  2640
gaaggctgta tgctgtttct cctggtatga gatagcgttt tggcctctga ctgacgctat  2700
ctcaccagga gaaacaggac acaaggcctg ttactagcac tcacatggaa caaatggcct  2760
ctagcctgga ggcttgctga aggctgtatg ctgccgcaaa gtctaagtac ttgggttttg  2820
gcctctgact gacccaagta cagactttgc ggcaggacac aaggcctgtt actagcactc  2880
acatggaaca aatggcctct ctagaataat caacctctgg attacaaaat ttgtgaaaga  2940
ttgactggta ttcttaacta tgttgctcct tttacgctat gtggatacgc tgctttaatg  3000
cctttgtatc atgctattgc ttcccgtatg gctttcattt tctcctcctt gtataaatcc  3060
tggttgctgt ctctttatga ggagttgtgg cccgttgtca ggcaacgtgg cgtggtgtgc  3120
actgtgtttg ctgacgcaac ccccactggt tggggcattg ccaccacctg tcagctcctt  3180
tccgggactt tcgctttccc cctccctatt gccacggcgg aactcatcgc cgcctgcctt  3240
gcccgctgct ggacaggggc tcggctgttg ggcactgaca attccgtggt gttgtcgggg  3300
aaatcatcgt cctttccttg gctgctcgcc tgtgttgcca cctggattct gcgcgggacg  3360
tccttctgct acgtcccttc ggccctcaat ccagcggacc ttccttcccg cggcctgctg  3420
ccggctctgc ggcctcttcc gcgtcttcgc cttcgccctc agacgagtcg gatctccctt  3480
tgggccgcct ccccgcctaa gcttatcgat accgtcgaga tctaacttgt ttattgcagc  3540
ttataatggt tacaaataaa gcaatagcat cacaaatttc acaaataaag catttttttc  3600
actgcattct agttgtggtt tgtccaaact catcaatgta tcttatcatg tctggatctc  3660
gacctcgact agagcatggc tacgtagata agtagcatgg cgggttaatc attaactaca  3720
aggaacccct agtgatggag ttggccactc cctctctgcg cgctcgctcg ctcactgagg  3780
ccgggcgacc aaaggtcgcc cgacgcccgg gctttgcccg ggcggcctca gtgagcgagc  3840
gagcgcgcag                                                    3850

SEQ ID NO: 20           moltype = AA  length = 125
FEATURE                 Location/Qualifiers
REGION                  1..125
                        note = Synthetic Sequence
source                  1..125
                        mol_type = protein
                        organism = synthetic construct
SEQUENCE: 20
MHVAQPAVVL ASSRGIASFV CEYASPGKYT EVRVTVLRQA DSQVTEVCAA TYMMGNELTF  60
LDDSICTGTS SGNQVNLTIQ GLRAMDTGLY ICKVELMYPP PYYEGIGNGT QIYVIDPEPC  120
PDSDQ                                                         125
```

The invention claimed is:

1. A composition comprising:

a. a nucleotide sequence encoding a belatacept-similar protein (BSP);

b. one or more nucleotide sequences encoding an micro-ribonucleic acid (miRNA) that targets messenger ribonucleic acid (mRNA) of tumor necrosis alpha (TNF-alpha); and c. an inverted terminal repeat.

2. The composition of claim 1, wherein the nucleotide sequence encoding BSP is SEQ ID No. 2.

3. The composition of claim 1, wherein the one or more nucleotide sequences encoding an miRNA are is one or more of SEQ ID No. 4, SEQ ID No. 5 and SEQ ID No. 6.

4. The composition of claim 1, wherein the inverted terminal repeat is SEQ ID No. 17, SEQ ID No. 18 or SEQ ID No. 19.

* * * * *